(12) United States Patent
Adie et al.

(10) Patent No.: US 10,197,379 B2
(45) Date of Patent: Feb. 5, 2019

(54) OPTICAL SENSING BASED ON MEASUREMENTS OF DISPLACEMENTS INDUCED BY OPTICAL FORCES IN VISCOELASTIC MEDIA USING PHASE-SENSITIVE OPTICAL COHERENCE TOMOGRAPHY

(71) Applicant: Cornell University, Ithaca, NY (US)

(72) Inventors: Steven Adie, Ithaca, NY (US); Gavrielle Untracht, Short Hills, NJ (US); Nichaluk Leartprapun, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/445,690

(22) Filed: Feb. 28, 2017

(65) Prior Publication Data

US 2017/0241765 A1 Aug. 24, 2017

Related U.S. Application Data

(63) Continuation-in-part of application No. 15/162,608, filed on May 23, 2016, now Pat. No. 10,072,920.

(60) Provisional application No. 62/165,855, filed on May 22, 2015.

(51) Int. Cl.
*G01B 9/02* (2006.01)
*A61B 5/00* (2006.01)

(52) U.S. Cl.
CPC ........ *G01B 9/02091* (2013.01); *A61B 5/0066* (2013.01); *G01B 9/02002* (2013.01); *G01B 9/02012* (2013.01); *G01B 9/02015* (2013.01)

(58) Field of Classification Search
CPC ............ G01B 9/02091; G01B 9/02015; G01B 9/02012; G01B 9/02002; A61B 5/0066
See application file for complete search history.

(56) References Cited

U.S. PATENT DOCUMENTS 8,002,480 B2 8/2011 Polster
2016/0341539 A1 11/2016 Adie et al.

OTHER PUBLICATIONS

Zhang, H.F. eet al., "Functional photoacoustic microscopy for high-resolution and noninvasive in vivo imaging", Nature Biotechnology, 2006, 24(7), pp. 848-851.
Zhao, R.G. et al., "Magnetic approaches to study collective three-dimensional cell mechanics in long-term cultures (invited)", Journal of Applied Physics, 2014, 115(17).
Paszek, et al. "Tensional homeostasis and the malignant phenotype", Cancer Cell, 2005, 8(3): p. 241-254.

(Continued)

*Primary Examiner* — Hwa Lee
(74) *Attorney, Agent, or Firm* — Perkins Coie LLP

(57) ABSTRACT

A system for providing optical actuation and optical sensing can include an optical coherence tomography (OCT) device that performs optical imaging of a sample based on optical interferometry from an optical sampling beam interacting with an optical sample and an optical reference beam; an OCT light source to provide an OCT imaging beam into the OCT device which splits the OCT imaging beam into the optical sampling beam and the optical reference beam; and a light source that produces an optical actuation beam comprising a plurality of wavelengths that is coupled along with the optical sampling beam to be directed to the sample to actuate particles or structures in the sample so that the optical imaging captures information of the sample under the optical actuation.

20 Claims, 21 Drawing Sheets

(56) References Cited

OTHER PUBLICATIONS

Adie, S.G. et al., "Spectroscopic optical coherence elastography", Optics express, 2010, vol. 18, No. 25, pp. 25519-25534.
Adie, S.G. et al., "Computational adaptive optics for broadband optical interferometric tomography of biological tissue", Proceedings of the National Academy of Sciences of the United States of America, 2012, 109(19), p. 7175-7180.
Adie, S.G. et al., "Guide-star-based computational adaptive optics for broadband interferometric tomography", Applied Physics Letters, 2012, 101(22).
Ahmad, A., et al., "Real-time in vivo computed optical interferometric tomography", Nature Photonics, 2013, 7(6), p. 445-449.
Ashkin, A., "Acceleration and trapping of particles by radiation pressure", Physical Review Letters, 1970, 24, p. 156.
Bezryadina, A. et al. "Optical manipulation of rod-shaped bacteria and adhesive cellular clusters with novel tug-of-war optical tweezers," CLEO: 2014, OSA Technical Digest (online) paper SF1H.2, 2014.
Bloom, R.J. et al., "Mapping local matrix remodeling induced by a migrating tumor cell using three-dimensional multiple-particle tracking", Biophysical Journal, 2008, 95(8), p. 4077-4088.
Boppart, S.A. et al., "In vivo cellular optical coherence tomography imaging", Nature Medicine, 1998, 4(7), p. 861-865.
Bowman, R et al. "Optical Trapping and Binding", Reports on Progress in Physics, 2013, 76(2).
Butcher et al., "A tense situation: forcing tumour progression", Nature Reviews Cancer, 2009, 9(2), pp. 108-122.
Carey, S. et al.., "Leading malignant cells initiate collective epithelial cell invasion in a three-dimensional heterotypic tumor spheroid model", Clinical and Experimental Metastasis, 2013, 30(5), pp. 615-630.
Chang, E.W. et al., "Subnanometer optical coherence tomographic vibrography", Optics Letters, 2012, 37(17), p. 3678-3680.
Chen, F.Y. et al., "A differentially amplified motion in the ear for near-threshold sound detection", Nature Neuroscience, 2011, 14(6), p. 770-U366.
Chen, Y. et al., "Measuring collective cell movement and extracellular matrix interactions using magnetic resonance imaging", Scientific Reports, 2013, 3.
"Chen, Z., ""Volume holographic microscopy for holographic 3D particle manipulation,"" Frontiers in Optics 2014, OSA Technical Digest (online), paper FTu1F.1, 2014."
Chen, Z., et al. "Real-time 3D particle manipulation visualized using volume holographic gratings," Optics Letters, 39(10), 3078-3081, 2014.
Chiou, P.Y. et al., "Massively parallel manipulation of single cells and microparticles using optical images," Nature Letters, 2005, 436.
Chow, T.H. et al., "Resolving interparticle position and optical forces along the axial direction using optical coherence gating", Applied Physics Letters, 2010, 97(23).
Dean-Ben, X. et al., "Volumetric real-time tracking of perpheral hu,a vasculature with GPU-accelerated three-dimensional optoacoustic tomography", IEEE Transaction on Medical Imaging, 2013, 32(11).
Divitt, S. et al., "Cancellation of non-conservative scattering forces in optical traps by counter-propagating beams", Optics Letters, 2015, 40(9).
Drexler, W., "Ultrahigh-resolution optical coherence tomography", Journal of Biomedical Optics, 2004, 9(1), p. 47-74.
"Dubin-Thaler, B.J. et al., ""Quantification of Cell Edge Velocities and Traction Forces Reveals Distinct Motility Modules during Cell Spreading"", PLoS One, 2008, 3(11)."
Fatemi, M. et al., "Vibro-acoustic tissue mammography", IEEE Transactions on Medical Imaging, 2002. 21(1): p. 1-8.
Fercher, A.F. et al., "Optical coherence tomography—principles and applications", Reports on Progress in Physics, 2003, 66(2), p. 239-303.
Fritsch, A. et al., "Are biomechanical changes necessary for tumour progression?", Nature Physics, 2010, 6(10), p. 730-732.

Fujimoto, J.G., "Optical coherence tomography for ultrahigh resolution in vivo imaging", Nature Biotechnology, 2003, 21(11), p. 1361-1367.
Gittes, F. et al., "Microscopic viscoelasticity: Shear moduli of soft materials determined from thermal fluctuations", Physical Review Letters, 1997, 79(17), p. 3286-3289.
Greenleaf, J.F. et al., "Ultrasound stimulated vibro-acoustography", Computer Vision and Mathematical Methods in Medical and Biomedical Image Analysis, 2004, 3117, p. 1-10.
Grier, D., "A revolution in optical manipulation," Nature, 2003, 424.
Haga, H. et al., "Elasticity mapping of living fibroblast by AFM and immunofluorescence observation of the cytoskeleton", Ultramicroscopy, 2000, 82(104), pp. 253-258.
Hanahan et al., "Hallmarks of cancer: the next generation", Cell, 2011, 144(5), pp. 646-674.
Hu, S. et al., "Second-generation optical-resolution photoacoustic microscopy with improved sensitivity and speed," Optics Letters, 36(7), 2011.
Huang, D. et al., "Optical Coherence Tomography", Science, 1991, 254(5035), p. 1178-1181.
John, RF. Et al., "In vivo magnetomotive optical molecular imaging using targeted magnetic nanoprobes", Proceedings of the National Academy of Sciences of the United States of America, 2010, 107(18), p. 8085-8090.
Kennedy, B.F. et al., "In vivo three-dimensional optical coherence elastography", Optics Express, 2011, 19(7), p. 6623-6634.
Kennedy, "Optical coherence micro-elastography: mechanical contrast imaging of tissue microstructure", Biomedical Optics Express, 2014, 5(7), pp. 2113-2124.
Kennedy, K.M. et al., "Optical Palpation: optical coherence tomography-based tactile imaging using a compliant sensor", Optics Letters, 2014, 39(10).
Kim, J.H. et al., "Propulsion and navigation within the advancing monolayer sheet", Nature Materials, 2013, 12(9), p. 856-863.
Kim, K. et al., "Simultaneous 3D visualization and position tracking of optically trapped particles using optical diffraction tomography," Optica, 2015, 2(4).
Koch, T.M. et al., "3D Traction Forces in Cancer Cell Invasion", PloS One, 2012, 7(3).
Kotlarchyk, M.A. et al., "Concentration independent modulation of local micromechanisms in a fibrin gel", PLoS One, 2011, 6(5).
Kotsifaki, D. et al., "Optical tweezers and manipulation of PMMA beads in various conditions," Proceedings of SPIE-OSA: Therapeutic Laser Applications and Laser-Tissue Interactions IV, R. Sroka and L. Lilge, eds., 7373, paper 7373_1V, 2009.
Kraning-Rush, C.M. et al., "Cellular Traction Stresses Increase with Increasing Metastatic Potential", PloS One, 2012, 7( 2).
Kraning-Rush, C.M. et al., "Quantifying Traction Stresses During Cell Migration", Methods in Cell Biology, 2012, 110, p. 139-178.
Kraning-Rush, C.M. et al., "The role of the cytoskeleton in cellular force generation in 2D and 3D environments", Physical Biology, 2011, 8(1).
Ladoux, B et al., "Physically based principles of cell adhesion mechanosensitivity in tissues", Reports on Progress in Physics, 2012, 75.
Legant, W.R. et al., "Measurement of mechanical tractions exerted by cells in three-dimensional matrices", Nature Methods, 2010, 7(12), p. 969-U113.
"Leventhal, et al., ""Matrix Crosslinking Forces Tumor Progression by Enhancing Integrin Signaling"""", Cell, 2009, 139(5), pp. 891-906."
Li, J. et al., "Dynamic optical coherence tomography measurements of elastic wave propagation in tissue-mimicking phantoms and mouse cornea in vivo", Journal of Biomedical Optics, 2013, 18(12), p. 121503.
Li, C.H. et al., "Quantitative elasticity measurement of urinary bladder wall using laser-induced surface acoustic waves", Biomedical Optics Express, 2014, 5(12), pp. 4313-4328.
Liang, X. et al., "Biomechanical Properties of In Vivo Human Skin From Dynamic Optical Coherence Elastography", IEEE Transactions on Biomedical Engineering, 2010, 57(4), p. 953-959.

(56) References Cited

OTHER PUBLICATIONS

Liang, X. et al. "Dynamic Spectral domain optical coherence elastography for tissue characterization", Optics Express, 2010, 18(13), pp. 14183-14190.
Liu, Y. et al., "Fiber Optical Tweezers for Cell Manipulation and Force Sensing," OSA Technical Digest Series (CD): Conference on Lasers and Electro-Optics/Quantum Electronics and Laser Science and Photonic Applications Systems Technologies, paper CMAA6, 2007.
Liu. et al., "Computed optical interferometric tomography for high-speed volumetric cellular imaging", Biomedical Optics Express, 2014, 5(9), p. 2988-3000.
Liu, L.B. et al., Imaging the subcellular structure of human coronary atherosclerosis using micro-optical coherence tomography, Nature Medicine, 2011, 17(8), p. 1010-U132.
Liu, Y. et al., "Investigation of inclined dual-fiber optical tweezers for 3D manipulation and force sensing," Optics Express, 2009, 17, pp. 13624-13638.
Liu, Y. et al., "Multiple traps created with an inclined dual-fiber system," Optics Express, 2009, 17, pp. 21680-21690.
Mahaffey, R.E. et al., "Scanning probe-based frequency dependant microrheology of polymer gels and biological cells", Physical review Letters, 2000, 85(4), pp. 880-883.
Manapuram, R.K. et al., "In vivo estimation of elastic wave parameters using phase-stabilized swept source optical coherence elastography", Journal of Biomedical Optics, 2012, 17(10).
"McGloin, D. et al., ""Forty Years of Optical Manipulation,"" Optics and Photonics News, 2010, 21(3), 20-26."
Mitri, F., "Arbitrary scattering of an electromagnetic zero-order Bessel beam by a dielectric sphere," Optics Letters 36, 766-768, 2011.
Mizuno, D. et al., "Active and Passive microrheology in equilibrium and nonequilibrium sysstems", Macromolecules, 2008, 41(19), pp. 7194-7202.
Mizuno, D. et al., "Nonequilibrium mechanics of active cytoskeletal networks", Science, 2007, 315(5810), p. 370-373.
Mohanty, S. et al., "Single-Fiber Optical Tweezers for Cellular Micro-Manipulation," Optics and Photonics News, 2008, 19(12), pp. 42-42.
Mohanty, S. et al., "Controlled induction, enhancement, and guidance of neuronal growth cones by use of line optical tweezers," Optics Letters, 2005, 30, pp. 2596-2598.
Muradoglu, M. et al. "Optical force lateral push—pulling using focus positioning," Journal of the Optical Society of America, 29, 874-880, 2012.
Nieminen, T.A. et al., "Physics of optical tweezers", Laser Manipulation of Cells and Tissues, 2007, 82, p. 207-236.
Nightingale, K. et al., "On the feasibility of remote palpation using acoustic radiation force", J. Acoust. Soc. of Am., 2001, 110(1), pp. 625-634.
Oldenburg, A.L. et al., "Resonant acoustic spectroscopy of soft tissues using embedded nanotransducers and optical coherence tomography", Physics in Medicine and Biology, 2010, 55(4), pp. 1189-1201.
"Orescanin, M. et al., ""Quantitative shear wave imaging of cell culture gels""", IEEE International Ultrasonics Symposium Proceedings, 2009."
Ott, D., et al. "Simultaneous three-dimensional tracking of individual signals from multi-trap optical tweezers using fast and accurate photodiode detection," Optics Express 22(19), 23661-23672, 2014.
Pacoret, C. et al., "Touching the microworld with force-feedback optical tweezers," Optics Express, 2009, 17, pp. 10259-10264.
Perch-Nielsen, I. et al., "Real-time interactive 3D manipulation of particles viewed in two orthogonal observation planes," Optics Express, 2005, 13, pp. 2852-2857.
Pesce, G. et al. "Step-by-step guide to the realization of advanced optical tweezers," Journal of the Optical Society of America, 32(5), 2015.
Provenzano, P.P. et al., "Collagen density promotes mammary tumor initiation and progression", BMC Medicine, 2008, 6(11).
Qi, W. et al., Resonant acoustic radiation force optical coherence elastography:, Applied Physics Letters, 2013, 103.
Ralston, T.S. et al. "Cross-validation of interferometric synthetic aperture microscopy and optical coherence tomography", Optics Letters, 2010, 35(10), p. 1683-1685.
Ralston, T.S. et al., "Interferometric synthetic aperture microscopy", Nature Physics, 2007, 3(2), p. 129-134.
Ralston, T.S. et al., "Interferometric synthetic aperture microscopy: Microscopic laser radar", Optics and Photonics News, 2010, 21(6), p. 32-38.
Razani, M. et al., "Biomechanical properties of soft tissue measurement using optical coherence elastography", Photonic Therputicss and Diagnostics VIII: Proceedings of SPIE, 2012, 8207(820758).
Razani, M. et al., "Optical coherence tomography detection of shear wave propagation in inhomogeneoud tissue equivalent phantoms and ex-vivo carotid artery samples", Biomedical Optics Express, 2014, 5(3), pp. 895-906.
Reffay, M. et al., Interplay of RhoA and mechanical forces in collective cell migration driven by leader cells (vol. 16, p. 217, 2014), Nature Cell Biology, 2014, 16(4), p. 382-382.
Serra-Picamel, X. et al., "Mechanical waves during tissue expansion", Nature Physics, 2012, 8(8), p. 628-U66.
Sitters, G. et al. "Acoustic force spectroscopy," Nature Methods, 12(1), 2015.
Solon, J. et al., "Fibroblast adaptation and stiffness matching to soft elastic substrates", Biophysical Journal, 2007, 93(12), p. 4453-4461.
Spyratou, E. et al., "Red blood cell micromanipulation with elliptical laser beam profile optical tweezers in different osmolarity conditions," Proceedings of SPIE-OSA:Medical Laser Applications and Laser-Tissue Interactions, V, R. Sroka and L. Lilge, eds., 8092, paper 80920T, 2011.
Stallinga, S., "Optical trapping at low numerical aperture", Journal of the European Optical Society-Rapid Publications, 2011, 6, p. 11027(1-8).
Suzuki, T., et al. "Enhancement of optical gradient force employed in optical tweezers using a pulsed laser diode," OSA Technical Digest (CD): Optics in the Life Sciences, paper OTMD4p, 2011.
Swaminathan et al., "Mecanical stiffness greades metastatic potential in patient tumor cells and in cancer cell lines", Cancer Research, 2011, 71(15), pp. 5075-5080.
Tambe, D.T. et al. "Collective cell guidance by cooperative intercellular forces", Nature Materials, 2011, 10(6), p. 469-475.
Trepat, X. et al., "Physical forces during collective cell migration", Nature Physics, 2009, 5(6), p. 426-430.
Trivedi, R. et al., "Three dimensional optical manipulation and structural imaging of soft materials by use of laser tweezers and multimodal nonlinear microscopy," Optics Express, 2010, 18, pp. 27658-27669.
Tucker-Schwartz, J.M. et al., "In vivo imaging of nanoparticle delivery and tumor microvasculature with multimodal optical coherence tomography", Biomedical Optics Express, 2014, 5(6), pp. 1731-1743.
Urban, M.W. et al., "A review of vibro-acoustography and its applications in medicine", Current Medical Imaging Reviews, 2011, 7(4), p. 350-359.
Van Der Horst, A. et al., "Calibration of dynamic holographic optical tweezers for force measurements on biomaterials," Optics Express, 2008, 16, pp. 20987-21003.
Van Der Horst, A. et al., "High trapping forces for high-refractive index particles trapped in dynamic arrays of counterpropagating optical tweezers," Applied Optics, 2008, 47, pp. 3196-3202.
Vedula, R.K. et al., "Collective Cell Migration: A Mechanistic Perspective", Physiology, 2013, 28(6), p. 370-379.
Wang, L. et al., "Fast voice-coil scanning optical-resolution photoacoustic microscopy", Optics Letters, 2011, 36(2), pp. 139-141.
Wang, R.K.K. et al., "Tissue Doppler optical coherence elastography for real time strain rate and strain mapping of soft tissue", Applied Physics Letters, 2006, 89(14), p. 144103.

(56) References Cited

OTHER PUBLICATIONS

Wirtz, D. eet al., "The physics of cancer: the role of physical interactions and mechanical forces in metastasis", Nature Reviews Cancer, 2011, 11(7), p. 512-522.

FIG. 4
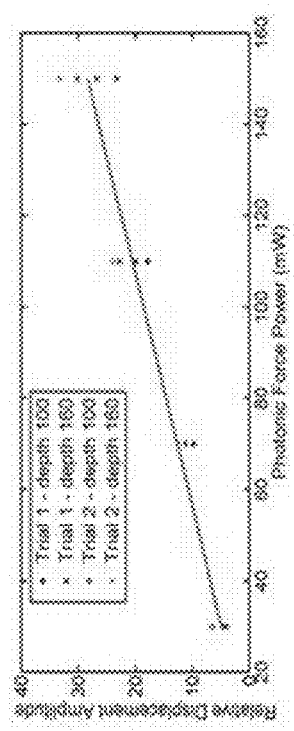
FIG. 4(a)
FIG. 4(b)
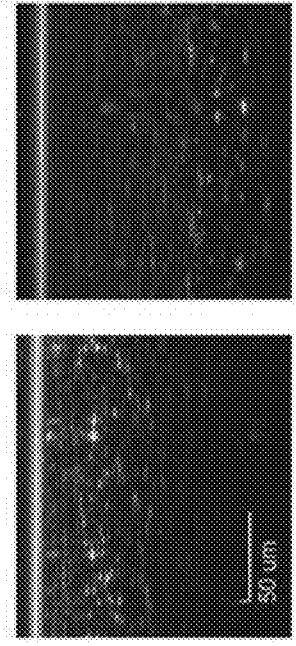
FIG. 4(c)
FIG. 4(d)
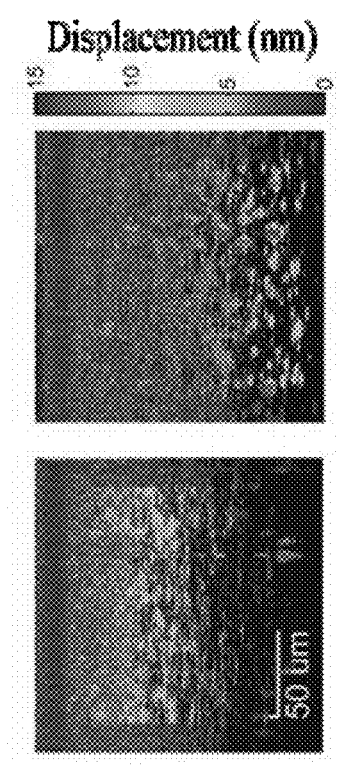
FIG. 4(e)
FIG. 4(f)

OPTICAL SENSING BASED ON MEASUREMENTS OF DISPLACEMENTS INDUCED BY OPTICAL FORCES IN VISCOELASTIC MEDIA USING PHASE-SENSITIVE OPTICAL COHERENCE TOMOGRAPHY

PRIORITY CLAIM AND RELATED PATENT APPLICATION INFORMATION

This patent document is a Continuation-in-Part Application of U.S. patent application Ser. No. 15/162,608 filed May 23, 2016, which in turn claims priority and benefits of U.S. Provisional Patent Application No. 62/165,855 entitled "MEASUREMENT OF DISPLACEMENTS INDUCED BY OPTICAL FORCES IN VISCOELASTIC MEDIA USING PHASE-SENSITIVE OPTICAL COHERENCE TOMOGRAPHY" and filed on May 22, 2015, the entirety of which is incorporated by reference.

TECHNICAL FIELD

This patent document relates to optical sensing or detection based on optical coherence tomography (OCT).

BACKGROUND

Optical sensing based on light can be used in various applications due to various features offered by interaction of light and matter. Optical coherence tomography (OCT) is one example of optical sensing for various applications including imaging tissues, chemical materials or biological materials.

SUMMARY

This patent document discloses devices and techniques and applications based on optical sensing or detection of a sample using optical coherence tomography (OCT) while applying a separate modulated light beam to the sample to cause an optical force onto the sample. This use of separate light to cause mechanical actuation in the sample is advantageous in that there is no physical contact with the sample and thus avoids various technical issues in mechanical actuation by contact of a mechanical or acoustic wave actuator or other contact-type actuators. The disclosed devices and techniques may be applied to various optical sensing applications including improving measurements in optical coherence elastography (OCE).

In one aspect, a system is disclosed for providing optical actuation and optical sensing and includes an optical coherence tomography (OCT) device that performs optical imaging of a sample based on optical interferometry from an optical sampling beam interacting with an optical sample and an optical reference beam; an OCT light source to provide an OCT imaging beam into the OCT device which splits the OCT imaging beam into the optical sampling beam and the optical reference beam; and a light source that produces an optical actuation beam that is coupled along with the optical sampling beam to be directed to the sample to actuate particles, or any other optically scattering structures, in the sample so that the optical imaging captures information of the sample under the optical actuation.

In another aspect, a method is disclosed for sensing an optical sample and this method includes operating an optical coherence tomography (OCT) device to obtain optical images of a sample based on optical interference of an optical sampling beam interacting with an optical sample and an optical reference beam from an OCT light source emitting light within an optical spectral band of different optical wavelengths; operating a light source to produce an optical actuation beam at an optical wavelength different from the light of the OCT light source; and directing the optical actuation beam along with the optical sampling beam to the sample to actuate particles, or any other optically scattering structures, in the sample so that the optical imaging captures information of the sample under the optical actuation.

Those and other aspects of the disclosed devices and techniques and their implementations and applications are described in greater detail in the drawings, the description and the claims.

BRIEF DESCRIPTION OF THE DRAWINGS

FIG. 4 shows experimental results obtained from the scattering-force-induced local sample vibrations in gelatin phantoms. FIGS. 4($a$) and 4($b$) show sample OCT images and FIGS. 4($c$) and 4($d$) are the corresponding vibration amplitude maps. FIG. 4($e$) shows a linear relationship between applied power and vibration amplitude. FIG. 4($f$) demonstrates the response when the position of the focus within the sample is translated. For focal depth 1, OCT image contains a saturation artifact because OCT focus was too close to the surface of the sample (data not shown).

FIG. 5($a$) shows an OCT image of bovine liver tissue, and FIG. 5($b$) shows vibration amplitude map reconstructed for 200 Hz excitation. The green arrow indicates when the scattering force laser was turned on, and the pink arrow indicates when it was turned off. The incident scattering force laser power was 120 mW. Nanometer-scale vibrations are clearly visible due to the turn on and off locations in the image, as well as the depth dependent vibration amplitude.

DETAILED DESCRIPTION

Tissue measurements based on elastography are based on quantitative imaging of the mechanical response of a target tissue and allow the clinical professional (or biomedical scientist) to use an elastography system as a tool to diagnose diseases that alter tissue mechanical properties, or for exploring how biological processes are influenced by mechanics. The dynamic range of Young's modulus varies by over two orders of magnitude among different types of healthy and diseased tissue and the quantification of biomechanical properties during disease progression by precision elastography measurements could lead to earlier diagnosis and improved treatment. In elastography, the mechanical response of tissue is imaged by mechanically loading the sample and measuring the resulting (spatially-localized) displacements. Based on the intuition afforded by palpation, "soft" regions of tissue will compress (or "strain") more than "stiff" regions. Optical coherence tomography (OCT) can be used as an effective imaging modality to quantify tissue displacements and the OCT measurements contain the mechanical loading characteristics, and impact the overall capabilities for imaging tissue biomechanics.

This patent document discloses, among others, devices and techniques that use an optical coherence tomography (OCT) system (1) to use a light source coupled to the OCT system to provide an optical actuation beam to a sample to exert an optical force to the sample to move the particles, or any other optically scattering structures, within the sample in response to the applied optical force, and (2) to use a separate OCT light source coupled to the OCT system to send an OCT optical imaging beam into the OCT system to perform optical imaging of the sample that is optically activated by the optical actuation beam. Various aspects of the disclosed OCT technology based on the optical activation of the sample can be implemented to provide various advantages. For example, different from some optical coherence elastography (OCE) systems where an OCT module is used for performing elastography measurements by using air puff, acoustic vibrations or other ways of mechanical actuation of the sample to cause sample displacements, the disclosed technology in this document combines non-contact or contact-free optical activation by a separate optical actuation beam that is directed to an area of the sample under illumination by the OCT sampling beam to perform optical coherence elastography (OCE) measurements. The combination of the OCT and the optical activation provides an all optical system for OCE measurements and is a less invasive way of performing OCE measurements. Various techniques can be used to provide highly sensitive OCE measurements by separating signal contributions from other effects such as thermal effects caused by local heating by the optical actuation beam. The phase-sensitive nature of the OCT can be used to improve the signal to noise ratio in OCE measurements.

Figure 1:
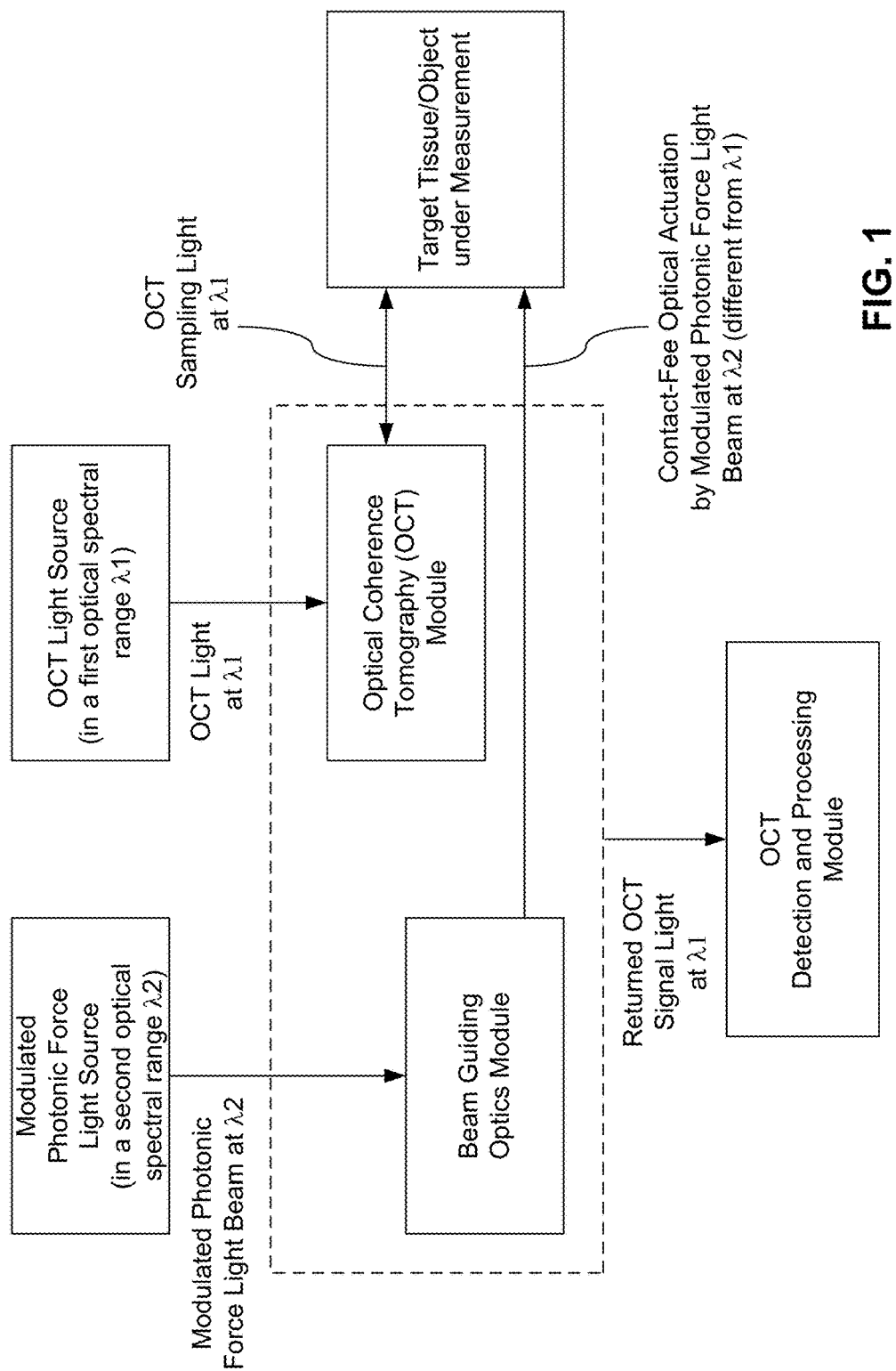
FIG. 1 shows an example of one implementation of an OCT system based on optical activation of the sample of the disclosed technology.
Figure 2:
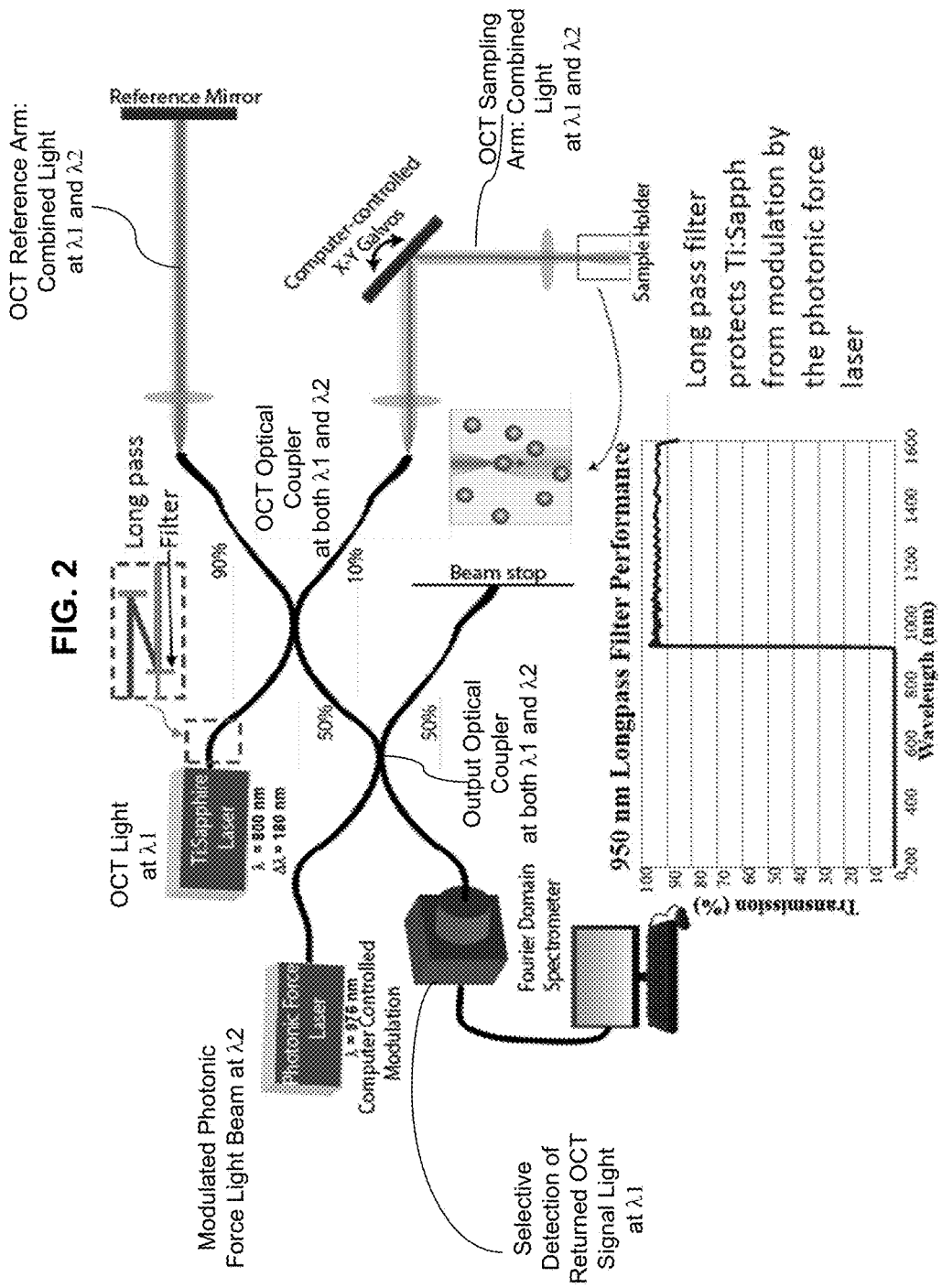
FIGS. 2 and 3 show two specific examples of OCT systems based on the configuration in FIG. 1.
Figure 3:
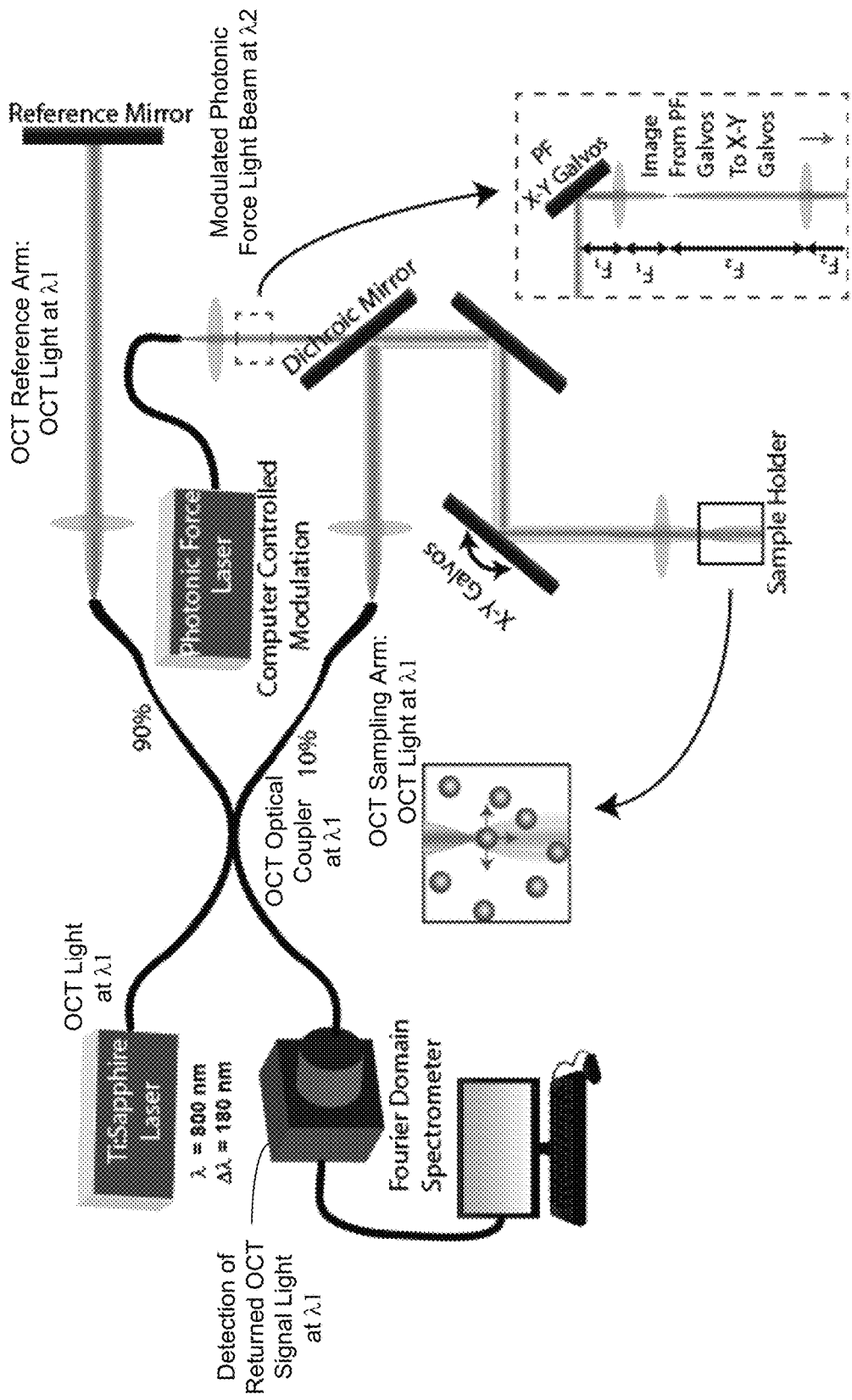

FIG. 1 shows an example of one implementation of an OCT system based on optical activation of the sample of the disclosed technology. This system includes two optical submodules that integrated with each other: (1) an OCT optical module to direct an OCT sampling beam (in a spectral range represented by $\lambda 1$) to the target sample for OCT imaging to interact with the sample and to acquire sample information based on optical interferometry, and (2) an optical activation module that performs optical actuation by using a separate optical actuation beam that is in a different spectral range represented by $\lambda 2$ and is directed to an area of the sample under illumination by the OCT sampling beam at $\lambda 1$. In this example, two separate light sources can be used to provide the OCT light at $\lambda 1$ and $\lambda 2$ and the optical actuation beam at $\lambda 2$ can be modulated in a suitable way to facilitate the OCE measurements. As illustrated, a beam guiding optics module can be used to direct the modulated optical actuation beam to the target sample such as a tissue area of a patient. The dashed box outside the beam guiding optics module and the OCT module represents the optical configuration of both modules where different optical arrangements are possible as shown in FIGS. 2 and 3. The returned OCT signal light at $\lambda 1$ can be extracted from the OCT module to be detected and processed in an OCT detection and processing module to generate the desired output representing the OCE data of the target sample.

In implementations, the OCT module can be in different configurations where the OCT light from the OCT light source as an OCT imaging beam into the OCT module which splits the OCT imaging beam into the optical sampling beam and the optical reference beam. The sampling beam and the reference beam may be spatially separated or may be partially overlap in their optical paths depending on the specific OCT configurations. Various OCT systems or configurations may be used to implement the disclosed OCT imaging and optical activation by using the first and second light sources, respectively. As an example, one of OCT system configurations uses two separate optical arms to form an optical interference between the light from the two optical arms where the light from a suitable OCT light source for OCT imaging (i.e., the second light source) is split into a sampling beam and a reference beam which propagate in two separate optical paths, the optical reference arm and the optical sampling arm, respectively. The light source may be partially coherent or low coherence light source to provide a broadband input light for OCT imaging based on broadband interferometry. The sampling beam is directed along the optical sampling arm to impinge on the sample under study, while the reference beam is directed in a separate path in the optical reference arm towards a reference surface. The sampling beam reflected from the sample and the reference beam reflected from the reference surface are then brought to spatially overlap with each other to optically interfere and the interference fringes or pattern of this interference can be used to obtain imaging information of the sample. A beam splitter may be used to split the light from the OCT light source and to combine the reflected sampling beam and the reflected reference beam for detection at an optical detector. FIGS. 2 and 3 illustrate OCT configuration examples in which the optical sampling beam and the optical reference beam are in different optical paths and do not spatially overlap except for at the optical coupler that splits the OCT light from the OCT light source into the two beams.

For optical actuation of the sample, an optical actuation beam produced by the first light source is coupled to the optical sampling arm of the OCT system to direct the optical actuation beam to the sample to exert an optical force to the sample to move the particles, or any other optically scattering structures, within the sample in response to the applied optical force. In some implementations, optical scattering forces are exerted by the optical actuation beam to induce localized vibrations, e.g., on the order of a few nanometers in viscoelastic gelatin or silicone phantoms and bovine liver. Detection via phase-sensitive OCT can be used to provide a novel approach for 3D cellular-resolution elastography.

FIG. 2 shows one example of an OCT for OCE measurements based on FIG. 1. The OCT light source is a Ti: Saphire laser at 800 nm with a laser operating spectral range of 180 nm. The optical actuation beam is a longer wavelength of around 976 nm and is modulated. In the OCT module, optical fiber paths are used to guide light in an optical interferometer configuration by using an OCT optical coupler: the OCT light at $\lambda 1$ from the OCT light source is first split by the OCT optical coupler into a reference upper beam (e.g., with 90% of the total power) and an OCT sampling lower beam (e.g., with 10% of the total power) to propagate in two separate fibers. The upper fiber path forms at least part of the optical reference arm as shown to include a fiber part and a free space optical path (with a lens and a reference mirror). The lower fiber path forms part of the sampling arm which includes a free space path that includes a lens, a X-Y scanner (such as a galvo scanner) for steering the sampling beam in the x and y directions over the sample for B-scan in the OCT operation and a second lens for focusing the OCT sampling beam into the target sample which is held by a sample holder. The optical actuation beam from the photonic force laser source at $\lambda 2$ can be directed along another fiber to an output optical fiber coupler that couples to the lower optical fiber in the OCT module. This output optical fiber couplers splits a portion of the light at $\lambda 2$ (e.g., 50% or another desired portion) into the lower optical fiber in the OCT module to reach the OCT optical coupler. The OCT optical coupler splits the light at $\lambda 2$ into two parts: one in the upper optical reference arm of the OCT and another in the lower optical sampling arm of the OCT to co-propagate with the OCT sampling beam at $\lambda 1$ to the sample. As such, the optical actuation beam at $\lambda 2$ and the OCT sampling beam at $\lambda 1$ spatially overlaps at the sample and are scanned at the same time along the x and y directions over the sample while the OCE measurements are being made. The returned OCT light at $\lambda 1$ from the reference and sampling arms meet and optically interfere at the OCT coupler to produce the OCT signal, a portion of which is coupled to the output optical coupler which directs it to an OCT detector which is shown as a Fourier domain spectrometer. In this design, the returned optical actuation light at $\lambda 2$ in both reference and sampling arms also meet and optically interfere at the OCT coupler and can be directed to the OCT detector. As part of the operation options, the returned optical actuation light at $\lambda 2$ may be filtered out at the OCT detector. In this design, the returned optical actuation light at $\lambda 2$ may be coupled by the OCT coupler back to the OCT light source (e.g., Ti: Saphire laser) to adversely affect the OCT light source operation. As shown, an optical filter or other optical isolation device can be used to eliminate this undesired optical feedback.

FIG. 3 shows another example of an OCT for OCE measurements based on FIG. 1. Similar to FIG. 2, the design in FIG. 3 uses a common x-y scanner (e.g., a galvanometer scanner) in the common optical paths of the OCT sampling beam at $\lambda 1$ and the optical actuation light at $\lambda 2$ to scan both beams together over the target sample for performing the B-scan OCT operation. Different from the design in FIG. 2, the OCT system in FIG. 3 injects the optical actuation light at $\lambda 2$ directly into part of the OCT sampling arm without getting the optical actuation light at $\lambda 2$ with other parts of the OCT module. Notably, in FIG. 3, a dichroic mirror that transmits optical actuation light at $\lambda 2$ and reflects the OCT light at $\lambda 1$ is used to inject the optical actuation light at $\lambda 2$ and to extract the returned optical actuation light at $\lambda 2$ so that optical actuation light at $\lambda 2$ may not be mixed with the OCT light at $\lambda 1$ in the rest part of the OCT module. Under this design, the returned OCT light at $\lambda 1$ from the reference and sampling arms meet and optically interfere at the OCT coupler to produce the OCT signal without being mixed with the returned optical actuation light at $\lambda 2$. As such, this design allows the optical actuation light at $\lambda 2$ to be directed at a spatially separate area of the sample from the OCT light at $\lambda 1$, and actuate the sample using optical gradient forces in addition to optical scattering forces. As shown by the dotted box upstream from the dichroic mirror, a second x-y scanner can be inserted in to the optical path of the optical actuation beam to steer the x and y positions of the optical actuation beam independently from the OCT sampling beam. Therefore, the foci of the optical actuation beam and OCT sampling beam may be deviated from one another. In FIG. 2, by comparison, the foci of the optical actuation beam and the OCT sampling beam should be precisely aligned in the transverse dimension in order to image the maximum possible displacement along the axial dimension and under this alignment the device in FIG. 2 is limited to only measuring the mechanical properties of the sample along one axis (the z-axis) and does not allow for the measurement of anisotropy of mechanical properties. The design in FIG. 3 with the capability of independently controlling the transverse positions in the x and y directions for the optical actuation beam and OCT sampling beam allows measurements of the mechanical anisotropy by adjusting the optical actuation beam transversely to move a bead or particle in the transverse dimension. This aspect of FIG. 3 allows it to take the advantage of the optical gradient forces typically used in optical tweezers.

In one implementation the device in FIG. 3 can be used to vary the transverse distance between the OCT and optical actuation beam, so as to apply time-varying transverse gradient forces to the particles, or any other optically scattering structures, within the sample. This transverse actuation of sample regions can be utilized to probe the mechanical properties of the sample along any axis in the transverse plane. When combined with the axial actuation provided by scattering forces applied by the optical actuation beam, this provides access to the three-dimensional anisotropic mechanical response of spatially localized regions within a sample.

In implementations, the example devices in FIGS. 2 and 3 can be used to achieve relatively high-frequency and wider bandwidth active microrheology (AMR) by amplitude modulating the photonic force beam at a high frequency (e.g., 20 kHz) to induce axial bead oscillations by optical scattering forces. In FIG. 3, transverse bead oscillations by the optical gradient force can also be induced by spatially separating the OCT light at λ1 and optical actuation light at λ2. Based on the needs of specific OCT imaging applications, the disclosed devices can be configured to support high-speed OCT acquisition, with high A-scan rates along the z direction (e.g., 100 kHz, leading to 1 mm×1 mm×1 mm volumetric acquisition time under a minute).

The above examples of OCT devices for OCE measurements based on optical actuation can be used to measure various samples. In some samples, the organization of the extracellular matrix (ECM) is highly regulated; cells are constantly remodeling their microenvironment in order to move and communicate with other cells. Recent research indicates that cellular-scale heterogeneity of the ECM plays a significant role in determining how cells behave, including tissue organization during development and how and where cells migrate. In addition, mechanical properties can be an important indicator of the diseased state of tissue. The disclosed technology such as the systems shown in FIGS. 1-3 can be configured to measure mechanical properties of tissue with cellular resolution.

Optical coherence elastography (OCE) is a promising technique for imaging the mechanical properties of tissue. Although OCT offers resolution down to the cellular scale, the methods of mechanical loading are applied over dimensions that are more than an order of magnitude larger than a cell. The optical actuation design in the disclosed technology here can be used for reducing the excitation volume to improve the mechanical resolution by decoupling the local mechanical response from the bulk response.

The disclosed combination of optical actuation and OCT imaging via the same OCT system can be used to provide a new OCE technique that uses optical scattering or gradient forces to excite localized vibrations in the sample. Previous work in the field of active microrheology has demonstrated that the viscoelastic properties of a sample can be characterized by inducing displacements using gradient forces of optical tweezers. In one implementation, the disclosed technology uses scattering forces, which are an order of magnitude smaller than gradient forces and are often undesirable in laser trapping experiments, to achieve improved OCE measurements. Notably, the optical actuation disclosed in this document, when combined with the subnanometer-scale displacement sensitivity of phase-sensitive OCT, can be used to detect these displacements. Additionally, the 3D localization of the excitation volume is controllable by selecting the numerical aperture (NA) of the scattering force beam or the optical activation beam.

Details of one implementation of such a system are provided in which the OCT system includes a Ti: Sapphire laser (Femtolasers, Integral Element) with 800 nm central wavelength, 188 nm bandwidth, and 120 mW output power (in optical fiber), corresponding to an axial resolution of 1.5 µm. The laser output is split into sample and reference signals using a 90:10 fiber coupler (Thorlabs, FC780-90B-APC). The OCT beam power incident on the sample was less than 10 mW. Images have a lateral resolution of approximately 3 µm. A gamma correction of 0.6 was also applied to the images.

To excite vibrations in the sample, a diode laser (Innovative Photonic Solutions, #I0976SB0500P) with a central wavelength of 976 nm and an output power up to 500 mW. The laser was amplitude modulated at a frequency between 10 Hz and 10 KHz to apply harmonic excitation. The laser was coupled into the OCT sample arm so that it was co-linear with the OCT beam, forming a similar focal spot size to the OCT beam.

Gelatin phantoms consist of 4% gelatin (bovine, Sigma Aldrich) cooked at 75 C for 1 hour, then mixed with ~10 mg/ml $TiO_2$ particles with an average diameter of 500 nm or 3 µm diameter polystyrene spheres and polymerized at room temperature. Silicone phantoms consist of 3000 parts or 2500 parts polydimethylsiloxane (Sigma Aldrich) and 10 parts and 1 parts cross-linking agent (GE RTV 615 A) and curing agent (GE RTV 615 B), respectively. The bovine liver sample was fresh from the butcher shop.

FIG. 4 shows experimental results obtained from the scattering-force-induced local sample vibrations in gelatin phantoms. In order to ascertain that the observed displacements are in response to the applied scattering force, we tested that the response changes as expected when the applied force profile is changed. We filtered the vibration amplitude map to include only frequencies near the excitation frequency of the applied force. This greatly improved the SNR of the vibration amplitude maps. Next, we tested that the vibration amplitude was linearly proportional to applied power using a 4% gelatin sample with a sparse concentration of 3 micron polystyrene spheres (FIG. 4(e)). We selected two beads near the focus and measured the relative height of the peak in the power spectrum at an excitation frequency of 100 Hz, and found that the vibration amplitude was directly proportional to the applied power. Next, we looked at the relationship between vibration amplitude and depth for various positions of the focus within the sample (FIG. 4). The photonic force power is 120 mW and the excitation frequency is 200 Hz. As the position of the focus is translated down into the sample, the location of peak vibration amplitude moves down accordingly. FIGS. 4(a) and (b) show examples of OCT images, and FIGS. 4(c) and 4(d) show the corresponding vibration amplitude maps for two focal positions within the sample. FIG. 4(f) shows the vibration amplitude vs depth averaged across all the rows of the image. Vibration amplitude data was fitted with a Gaussian beam profile.

Figure 5:
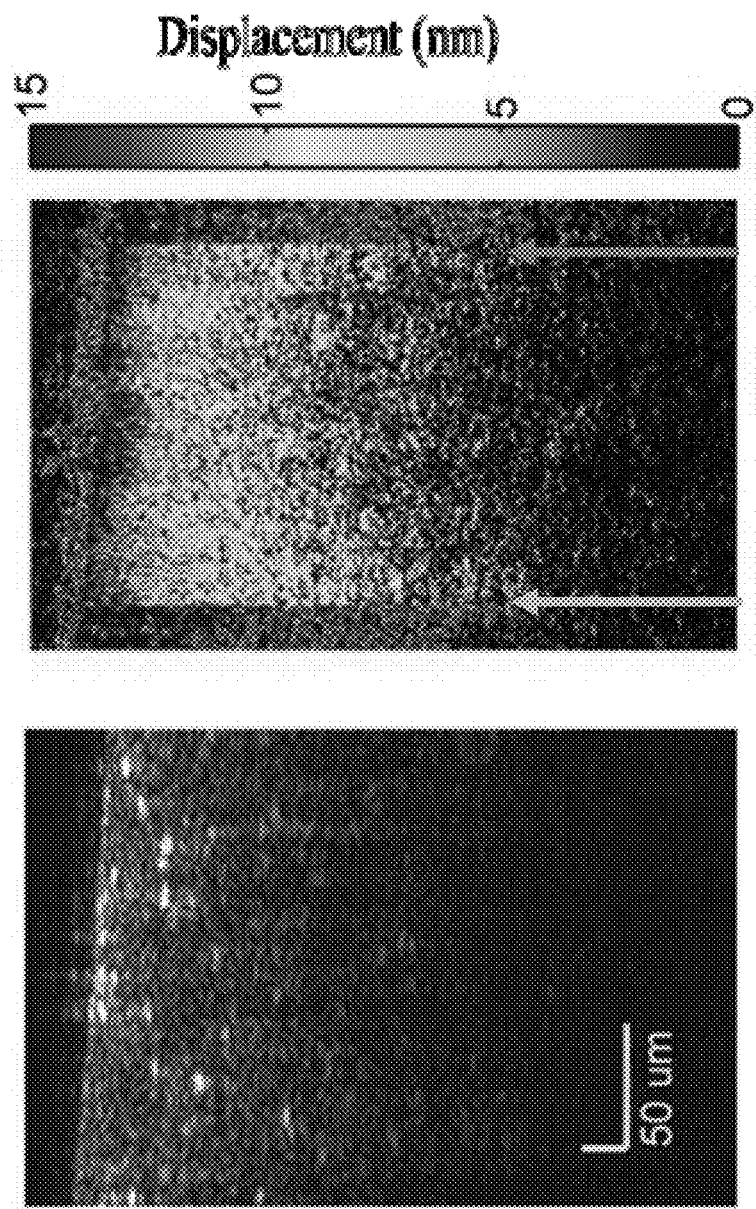
FIG. 5 shows experimental results from optical scattering force induced vibrations in scattering tissue.

FIG. 5 shows an example of vibrations induced in bovine liver tissue. Vibration amplitudes up to 15 nm were observed near the optical focus. The measured vibration amplitudes are small enough that phase-sensitive interferometric detection is required for accurate measurement. The turn-on and turn-off locations are clearly visible in the image, indicating a system displacement sensitivity (from region with the scattering force off) of ~1 nm. In addition, the vibration amplitude profile is depth dependent, as expected. Since the applied force is directly proportional to intensity, the applied force increases with depth until the focus is reached. Beyond the focus, the vibration amplitude is difficult to observe due to reduced SNR of the OCT images.

The disclosed technology and its implementations can be used for optical elastography technique for cellular-resolution volumetric imaging of extracellular matrix (ECM) mechanical properties during cancer cell migration and local invasion. The technology can address the need for new imaging capabilities that move beyond measures of 2D cellular forces, and enable 3D studies of single cell mechanics to expand into the analysis of collective behavior of migrating cell populations. This technology can be used to meet the need for long-range volumetric imaging of cancer mechanics with cellular resolution. In studies of the tumor microenvironment, it is important to obtain information on the mechanical properties of the tumor microenvironment, largely consisting of the ECM, in cancer initiation and development. It is known that the altered stiffness is not just a symptom of tumors, but can actually trigger the onset of malignancy. The research has also suggested 3D microenvironments (as opposed to 2D surfaces) are important to recapitulate key features of migratory behavior in vivo, motivating the use of 3D matrices in cancer mechanobiology research. Those developments in combination with the coordinated migratory behavior, and the recent discoveries of the role of long-range mechanical interactions in guiding the collective migration of cancer cell populations suggest that primary tumor formation involves growth from nominally isolated cancer cells into a large population of cells. Thus it is important to be able to study behavior on both the single-cell level as well as collective behavior over distances that are long with respect to a single cell Cancer cells can produce dramatically different migratory behavior in 3D versus 2D environments. The disclosed technology in this document provides such 3D imaging capabilities and can provide long-range volumetric measurements of collective mechanical behavior with cellular resolution. The disclosed technology in this document provides a method to perform the first 4D (3D spatial+time) imaging of tumor microenvironment mechanics during collective cell migration. By enabling (complete 4D) multi-dimensional investigations, the use of the disclosed technology could lead to a deeper understanding of potential spatiotemporal (physical) hallmarks of cancer, that can be used to develop earlier diagnostics, or to design and test new 'mechano-therapies' that target/modulate the mechanical properties of the ECM.

The disclosed technology based on OCT for OCE measurement by optical actuation can be used to address certain technical difficulty in using high numerical aperture (NA) laser tweezers-based microrheology methods to excite and detect transverse bead oscillations from $10^2$-$10^4$ beads distributed randomly within a 3D matrix. The disclosed technology can also be used to address the undesired results in various bulk excitation methods, e.g. via magnetic actuation of beads because the cumulative excitation of many beads results in bulk sample motion, rather than the highly localized excitation afforded by optical forces in this technology. The disclosed technology based on OCT for OCE measurement by optical actuation can use low-NA optical scattering forces to induce on-axis bead displacements rather than transverse bead displacements that are typical of existing laser tweezers-based active microrheology setups based on optical gradient forces. In some implementation, low-NA on-axis scattering forces may be about 1-2 orders of magnitude lower than the gradient forces of traditional high-NA laser tweezers, but advantageously can apply (transversely-localized) force over an extended depth range. Combining the subnanometer-scale displacement sensitivity of phase-sensitive OCT, computed imaging methods, and dynamic OCE techniques, the disclosed technology enables the use of OCT-based ultra-precise detection of photonic-force-induced bead displacements, coupled with cellular-resolution 3D mapping of bead positions over an extended depth range. Successful development of the disclosed technology can be enabling for the field of cancer mechanobiology, e.g., providing 4D imaging studies of microenvironment mechanics during single and collective cancer cell migration, enabling 4D imaging of leader-follower cell migratory behavior of tumor spheroids by adding 3D measurements of the dynamic mechanical properties.

Also, a significant advantage for volumetric imaging is that, unlike confocal microscopy, OCT does not rely on high numerical aperture (NA) for optical sectioning. Consequently, cellular and sub-cellular resolution imaging is possible at much lower NA, while advantageously allowing signal to be collected over a comparatively larger depth range. Since OCT systems measure both the amplitude and phase of backscattered light, computational image formation methods have been developed to address traditional limitations in the field of optical imaging, that are still present, even at lower NA. Interferometric synthetic aperture microscopy (ISAM) is a method, based on synthetic aperture radar (SAR), to reconstruct focal-plane resolution throughout a volumetric OCT dataset. In implementations, computational adaptive optics (CAO), a post-data-acquisition method to compensate optical aberration artifacts can be implemented in the disclosed technology and can be combined with ISAM to provide cellular resolution tomography over significantly larger volumes than previously possible.

Figure 6:
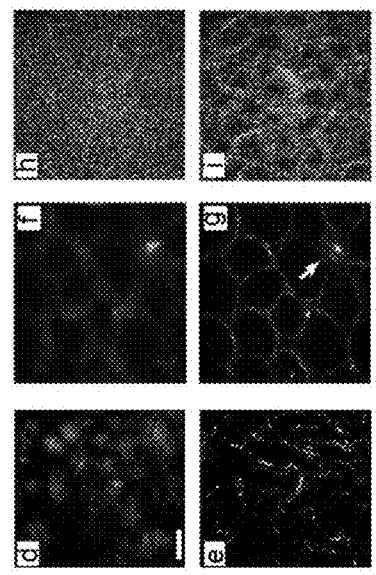
FIG. 6 shows that the disclosed OCT can provide cellular resolution volumetric imaging in tissue phantoms, in vitro cell cultures, and ex vivo or in vivo biological tissues, through the incorporation of methods for computational image formation, i.e. without having to scan the focus in depth.

Referring to FIG. 6, the disclosed OCT can provide cellular resolution volumetric imaging in tissue phantoms, in vitro cell cultures, and ex vivo or in vivo biological tissues, through the incorporation of methods for computational image formation, i.e. without having to scan the focus in depth. FIGS. 6(a-c) illustrate OCT and computational reconstructions (volume dimensions 256×256×1230 µm) of a silicone phantom seeded with 1 µm titanium-dioxide particles, and imaged with an astigmatic optical system, showing (a) OCT, (b) CAO, and (c) CAO+ISAM, respectively. FIG. 6 also shows cellular-resolution en face OCT images plus computational reconstructions of (d-e) mouse dermal fibroblasts in 3D macroporous alginate hydrogel scaffolds, showing (d) far-from-focus OCT image and (e) corresponding CAO+ISAM reconstruction, (e-f) human breast adipose tissue ex vivo, showing (f) far-from-focus OCT and (g) corresponding ISAM reconstruction (white arrow highlights a cell nucleus), (h-i) human skin (stratum granulosum layer) from epidermis of the palm in vivo, showing (h) far-from-focus OCT and (i) computationally refocused CAO+ISAM reconstruction (green arrow highlights one of the cell nuclei). The scale bar in (d) is 40 µm, and applies to images (d-i).

Another application of the disclosed technology is spectroscopic optical coherence elastography which generates images based on the underlying mechanical properties of tissue by applying a controlled mechanical loading ('palpation'), and then detecting the resulting displacements in the sample with OCT. These displacements are larger in soft (or compliant) tissue, and lower in hard (or rigid) tissue (such as tumors). One of the advantages of applying optical forces to the sample is that it allows highly localized actuation to be directed to precise coordinates within a three-dimensional sample. By controlling the numerical aperture of the actuation beam, the degree of localization in the axial and transverse dimensions can be controlled. One of the advantages of phase-sensitive interferometric detection with OCT is that it enables ultraprecise (nanometer-scale and below) displacement sensitivity. A measurement of the dynamic mechanical response of a sample allows both its elastic and viscous properties to be probed. Since water is a major constituent of many biological tissues, it is not surprising that the mechanical response of tissues is, in general, viscoelastic. The use of dynamic excitation is also of interest because it can provide more comprehensive information (than static methods) about tissue properties over a spectrum of frequencies. Dynamic methods are also better suited to in vivo application than static methods due to their reduced susceptibility to the inherent micron-scale physiological sample motion. Indeed, in vivo elastography via phase-sensitive OCE has to-date only been demonstrated using dynamic excitation. This ability of dynamic methods to move away from the dominant low-frequency phase noise of an OCT system is facilitated by the active (dynamic) microrheology approach in the disclosed technology.

Figure 7:
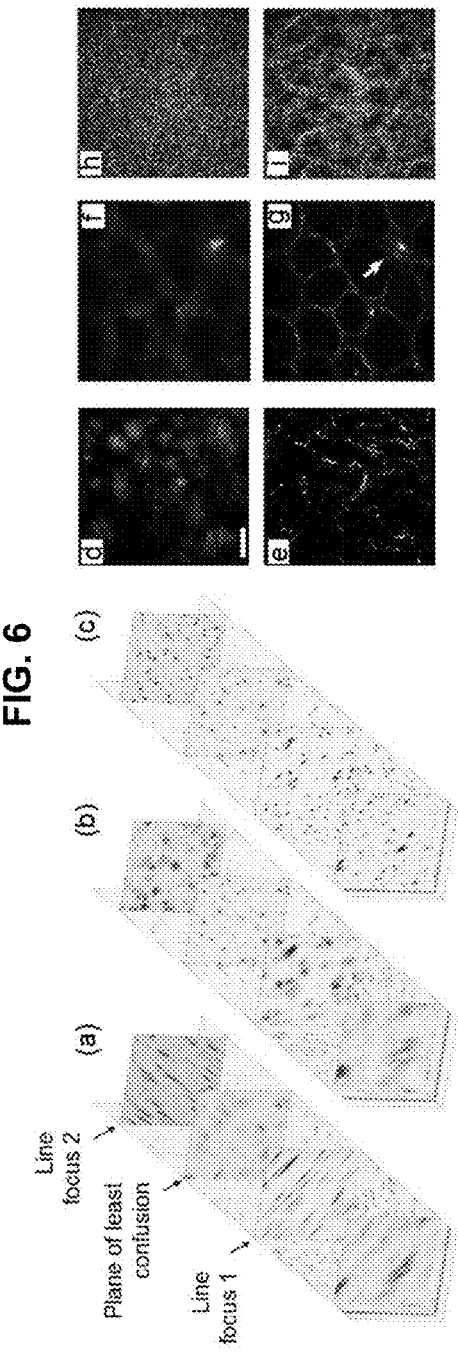
FIG. 7 shows spectroscopic OCE of a rat mammary tumor margin ex vivo.
Figure 7:
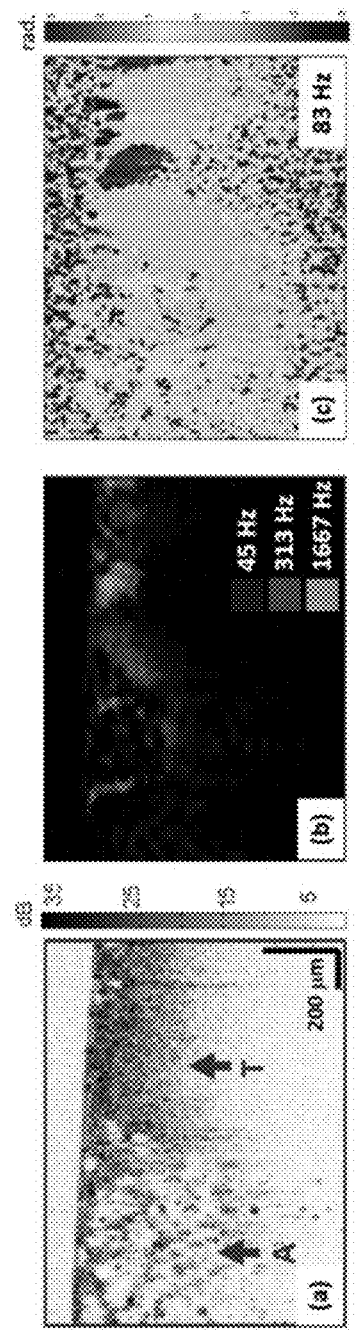

FIG. 7 shows spectroscopic OCE of a rat mammary tumor margin ex vivo. (a) OCT image (A=adipose, T=tumor), (b) relative displacement amplitudes, (c) displacement phase highlighting an oval structure attributed to a fluid-filled follicle. The disclosed technology can be used to achieve spectroscopic OCE, acquiring 3D data cubes comprising 2D B-mode images recorded over excitation frequencies spanning 20-1000 Hz. FIG. 7(c) shows the frequency-dependent provided contrast of spectroscopic OCE in rat mammary (tumor and adipose) tissue. As a striking example of enhanced image contrast, the mechanical phase image highlighted an oval region of the sample. This feature resembled oval-shaped structures in the histology image, and was attributed to being a fluid-dense follicle or vacuole.

The disclosed technology can be implemented by using laser tweezers-based active microrheology. Microrheology methods probe the local viscoelastic properties of a medium by observing the motion of micrometer-sized beads (typically polystyrene) within the medium. Micrometer-sized beads only have weak inertial effects, allowing their motions to be characterized over a wide frequency range (spanning 0.1 Hz to 100 kHz), thus providing wideband information about the characteristic timescales of interaction between the bead and its microenvironment. Passive microrheology (PMR) monitors fluctuations of bead position due to internal forces (that cause Brownian motion of the bead), and makes use of the fluctuation-dissipation theorem together with the Stokes formula to determine the complex shear modulus. In contrast, active microrheology (AMR) dynamically actuates these beads by applying external harmonic forces, often through the use of laser tweezers. The shear modulus of the medium can be determined similarly to PMR, after first accounting for the laser trap forces. AMR can be better suited than PMR to cancer cell mechanics research since the usefulness of passive measurements is limited, particularly at high frequencies and for stiff substrates. The disclosed technology can use phase-sensitive OCT detection and processing routines to extract the frequency-dependent displacements excited during wide-band AMR.

Optical radiation forces are the result of conservation of momentum (which is a vector quantity, i.e. has both magnitude and direction). Gradient forces are generated when a spherical bead acts as a 'mini-lens' to change the divergence of an optical beam that is incident on it. This 'focusing' effect (greatest at the highest intensity gradient of the beam) changes the momentum of the photons in the beam, and therefore results in a transfer of this momentum to the bead. Gradient forces act in 3D to move the bead toward the beam focus, since it is at the focus that the bead minimally impacts the beam divergence (momentum diversity of photons). Scattering forces result from optical scattering (superposition of reflections from the refractive index 'jump' at the surface of the bead), and produce a net 'radiation pressure' in the propagation direction of the beam. Typically, high-NA laser beams are utilized for optical manipulation since a smaller focus provides higher forces, due to both the increased photon density and larger intensity gradients. In the next section we provide simulations of axial gradient and scattering forces, and justify our intended use of low-NA optical scattering forces.

Low-NA optical scattering forces can be used in implementing the disclosed technology. Conventional, high-NA, gradient force-based laser trapping can produce ~60 nm bead displacements in viscoelastic fibrin gels, where AMR was employed to measure shear moduli in the range $10^2$-$10^3$ Pa. The optical trap stiffness in this study was 30 pN/µm, and a simple calculation (using 60 nm displacements) estimates peak forces of ~2 pN. Under the disclosed technology, low-NA optical scattering forces can be used to actively drive bead oscillations in tissue-like viscoelastic media. For the sake of performing a conservative calculation, we choose to excite harmonically driven oscillations with peak displacements between OCT A-scans of 100 nm, for a bead oscillation frequency of 500 Hz and an OCT A-scan rate of 5 kHz. Utilizing a bead diameter of 2 µm, and assuming $G\approx10^3$ Pa, we calculate that we will need peak photonic forces on the order of 1 pN. For a 976 nm photonic force laser with and a focused beam of NA ~0.1, our theoretical simulations (see FIG. 8) predict that we will need optical power within the range 10-200 mW. This suggests that we will be able to detect displacements in low-scattering homogeneous media with stiffness up into the few kPa range.

Figure 8:
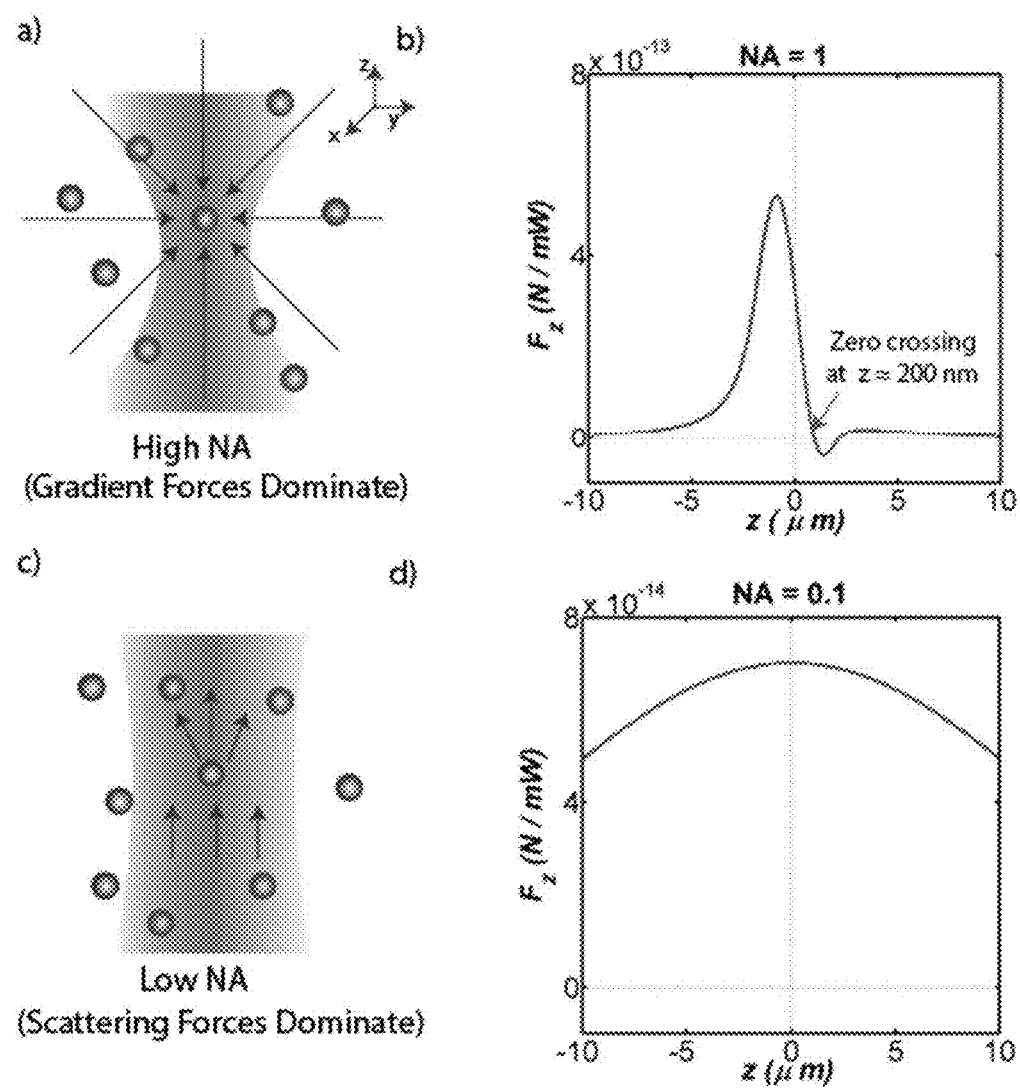
FIG. 8 shows theoretical simulations on the dependence of optical forces on the NA of the beam.

FIG. 8 shows theoretical simulations on the dependence of optical forces on the NA of the beam. At high NA (top row) gradient forces dominate, whereas at low NA (bottom row) scattering forces dominate. (a) High-NA (NA=1) laser trapping, (b) axial scattering force computed using an optical tweezer model. (c) Low-NA (NA=0.1) scattering forces, (d) axial scattering force computed using the low-NA treatment. As seen in (d) vs. (b), a low-NA beam can provide a consistent (albeit lower) force to beads over an extended depth range.

The disclosed technology based on OCT for OCE measurements by optical actuation can implement various techniques to improve the sensing performance. For example, the technology can be configured based on methods of distinguishing or isolating mechanical response and thermal response from the experimentally observed response, which includes contribution of both to variable extents. The observed sample response is a linear combination between the thermal (also referred to as 'photothermal') and mechanical response of the sample. In order to utilize this method to measure displacements due to optical scattering force, it is desirable to distinguish between these two components of the response. This may be accomplished by one or more of the following techniques.

Figure 9:
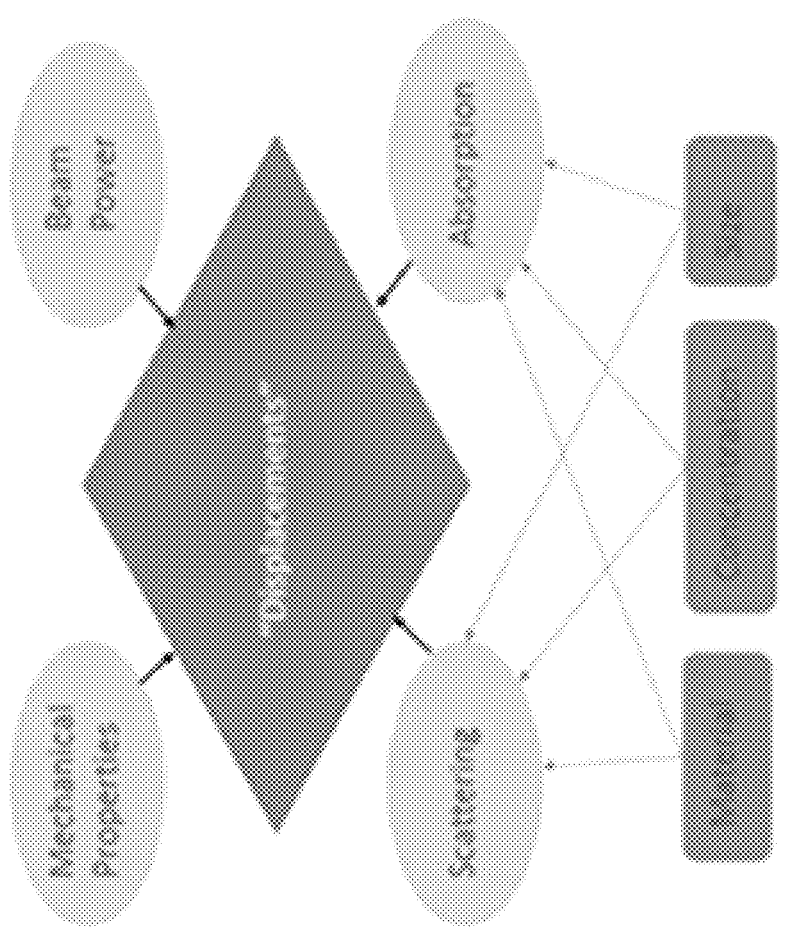
FIG. 9 shows a chart illustrating factors that can impact observed displacement (yellow circles) and materials properties that may modulate these factors (orange boxes).

One of the techniques is developing samples or experimental procedures such that all properties that may impact the observed 'displacements' (absorption, scattering, stiffness, and beam power) are held constant except one. FIG. 9 shows a chart illustrating factors that can impact observed displacement (yellow circles) and materials properties that may modulate these factors (orange boxes). Some examples of possible implementations include:

Varying beam power only. While at first glance it may seem like both the thermal and mechanical responses will scale linearly with applied power, this many not necessarily be true depending on the modulation frequency. Therefore, the spectroscopic response may differ as the beam power varies.

Varying mechanical properties only. Only the mechanical response can distinguish between samples with different mechanical properties. Demonstrating differences in displacement in samples with varying mechanical properties but identical optical absorption properties will be a clear indication that the observed response is a result of physical displacements.

Varying sample scattering only. Only the mechanical response will depend on optical scattering.

Varying sample absorption only. Only the thermal response will depend on optical absorption.

Figure 10:
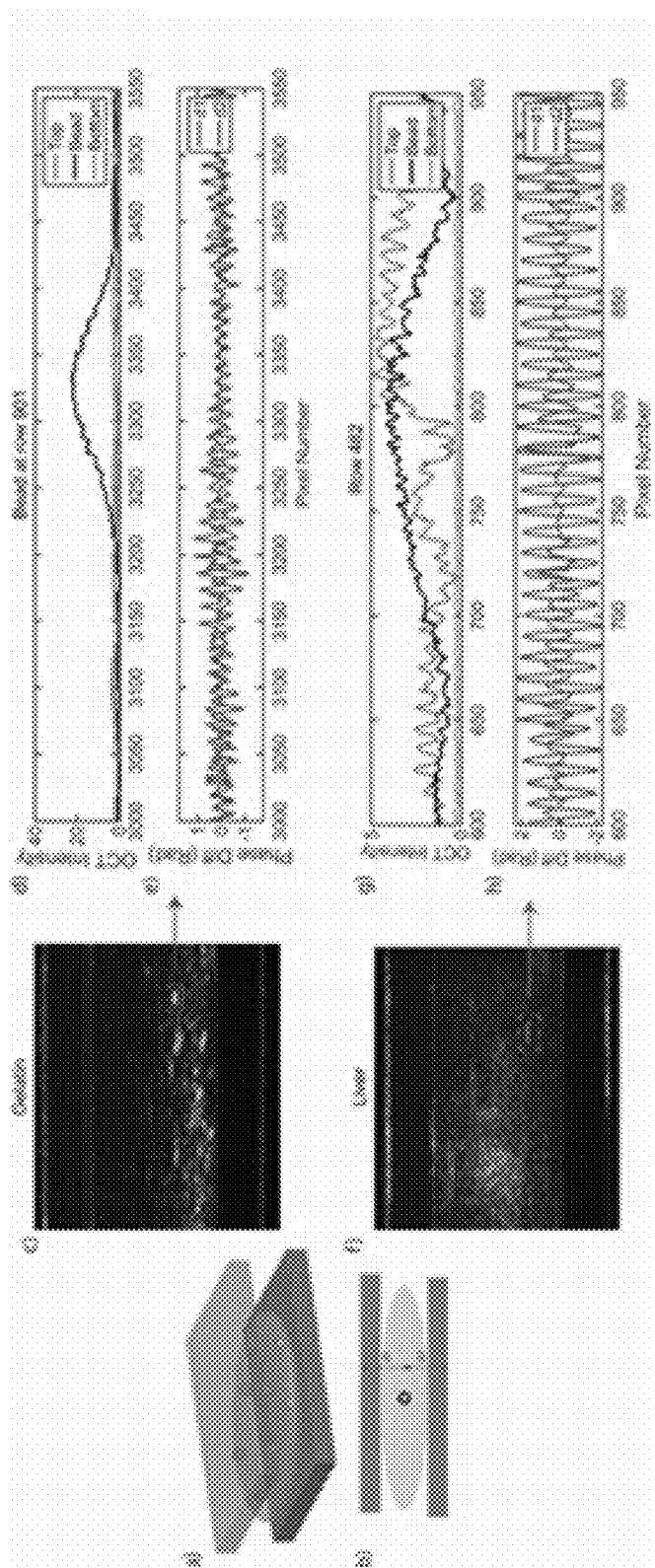
FIG. 10 shows a sandwich setup by placing a thin sample sandwiched between two coverslips FIG. 11 show plots of observed displacements (left) induced by various optical scattering force excitation schemes and their corresponding power spectrums (right). Red dotted lines mark the modulation frequency on the power spectrums.

FIG. 10 shows a sandwich setup by placing a thin sample sandwiched between two coverslips. Upon imaging the bead using the methods described here, the distance between the bead and the top surface and the distance between the bead and the bottom coverslip can be measured. The measurements can be used to plot the variation of these two quantities over time. If the distances oscillate in phase with each other, the sample is experiencing isotropic thermal expansion. If the two distances oscillate out of phase, the bead is oscillating within the sample. The phase shift between the two waveforms could be used to determine the relative contributions of the thermal and mechanical responses.

In detail, FIG. 10 shows the isotropy of OPL changes around a bead. FIG. 10(a) shows the sandwich sample geometry used for these experiments, and FIG. 10(b) shows a cross sectional view. The top row shows the results for a gelatin phantom, and the bottom row shows the results for liver. FIGS. 10(c) and 10(f) are the structural OCT images. FIG. 10(d) is the OCT signal intensity through the center of the scatterer in the pink box. FIG. 10(e) is the distance to the top and bottom coverslip. FIG. 10(g) is the signal intensity through the scattering maximum in the green box, and FIG. 10(h) is the distance to the top and bottom coverslip from this location. For the gelatin dataset, d1 and d2 have varying alignment, but are in phase in the region of high SNR at the bead location. This seems to imply that thermal effects are primarily responsible for the response. However, the liver dataset shows d1 and d2 oscillating mostly out of phase near the focus of the photonic force beam. This would seem to indicate that photonic force is primarily responsible for the effects.

Yet another technique is to isolate either the mechanical or the thermal response from the acquired data given that the other can be predicted from a priori information. This technique may involve:

Using previously characterized material properties such as predicting the thermal response of water in a primarily aqueous sample (e.g. biological tissues). The mechanical response of said sample may be isolated by subtracting the model of water absorption thermal response from the experimentally observed response.

Measuring either the optical absorption or optical scattering properties of the materials. This may be accomplished by using a spectrophotometer for an optically clear samples.

Designing the data acquisition scheme to capture the properties where thermal response and mechanical response are unique, such as Modulation frequency-dependence on the magnitude of the response, Modulation frequency-dependence on the phase of the response, or the characteristic time constants of the response, such as the heating time constant or the mechanical creep time constant.

In one implementation, measurements were taken on a silicone phantom under various optical scattering force excitation schemes: a step response, and harmonic responses at modulation frequencies ranging from 20 Hz to 100 Hz. Both the magnitude and phase of the observed displacements induced by each excitation scheme can be combined to construct the mechanical spectroscopic response of the sample.

Figure 11:
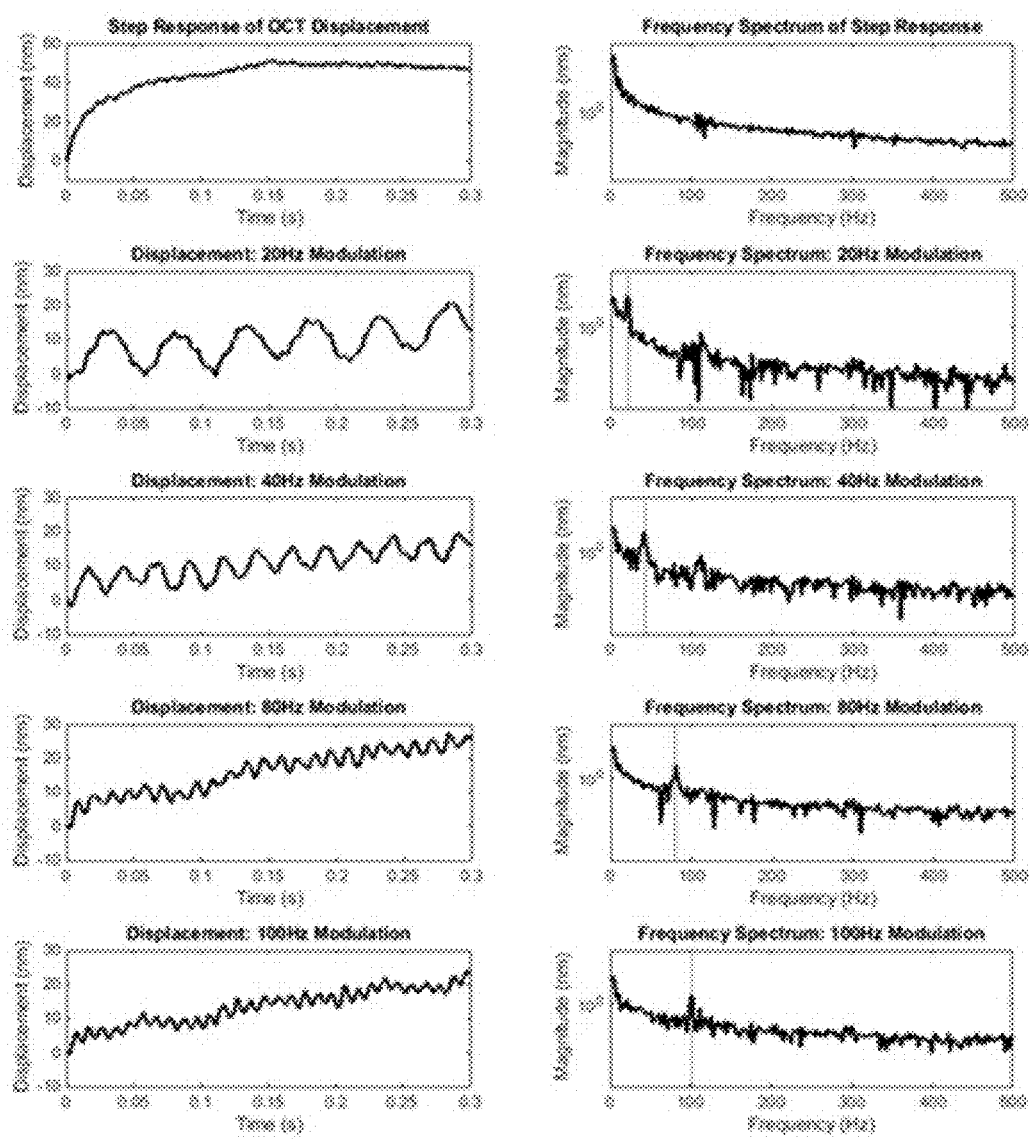

FIG. 11 show plots of observed displacements (left) induced by various optical scattering force excitation schemes and their corresponding power spectrums (right). Red dotted lines mark the modulation frequency on the power spectrums.

Figure 12:
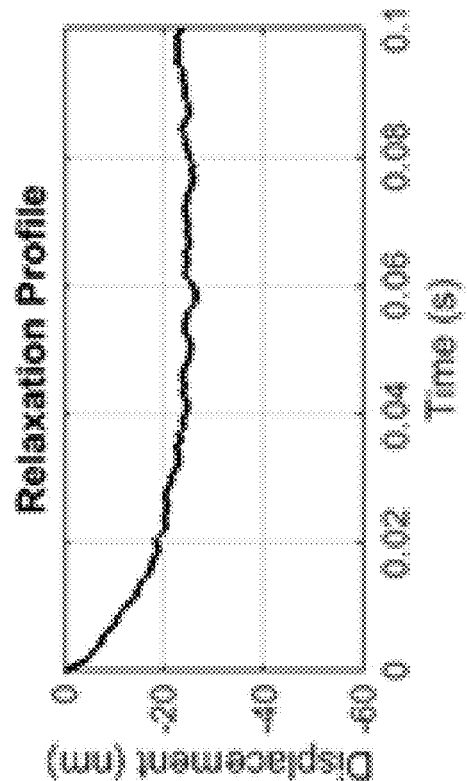
FIG. 12 shows an example of measurements of the Creep profile and relaxation profile of a soft silicone phantom measured during and after the application of a step optical scattering force.
Figure 12:
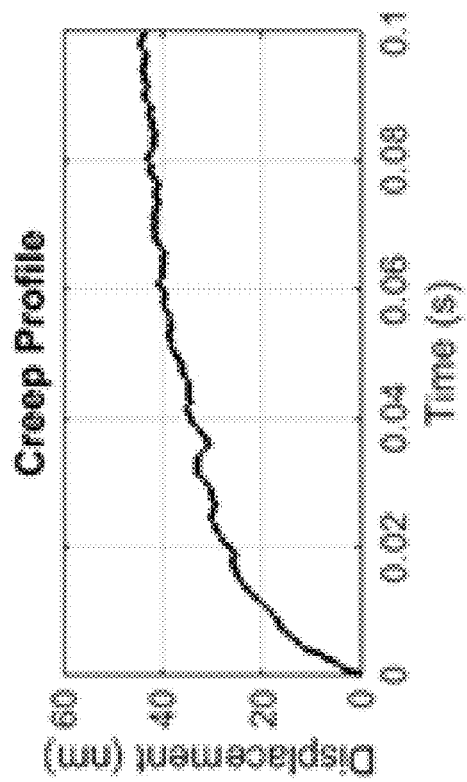

Regarding the characteristic time constants of the response, in one implementation, a silicone phantom can be excited by a step optical scattering force, during which the creep profile is measured. The force can be then turned off and the relaxation in the displacement is measured. The creep deformation and relaxation time constants may be determined from the time trace of the displacements. FIG. 12 shows an example of measurements of the Creep profile and relaxation profile of a soft silicone phantom measured during and after the application of a step optical scattering force. These curves may be fitted to a mathematical function to determine the characteristic time constant of the profile.

Designing the data acquisition scheme to capture the properties where thermal response and mechanical response are unique may also use additional techniques, such as location of system resonant frequency, scattering intensity-dependence on the magnitude of the response, wavelength-dependence of the interferometric signals of optical absorption versus scattering, or depth-dependence of the magnitude of the response, where thermal response accumulates with increasing depth below the optical focus while mechanical response decays in either direction away from the optical focus.

In another implementation, the wavelength of the optical actuation beam is varied over a given range, to acquire the optical-wavelength-dependent actuation response of the sample. This wavelength-dependent response curve may be fitted to a mathematical function that depends on the optical scattering and absorption properties of the sample, in order to determine the contribution of the mechanical response (which depends on forces applied by the actuation beam) and the thermal response (which depends on the absorption of the actuation beam by the sample).

In another implementation, the mechanical response of the sample to the actuation beam is perturbed by applying a controlled force preload to the sample using a contact-type or acoustic wave. The resulting perturbation to the detected sample response can then be interpreted as being due to the mechanical response rather than the thermal response of the sample. In one implementation, a preload force can be applied by mechanically actuating an optically transparent window that is in contact with the sample surface, such that the OCT and the photonic force optical actuation beam are transmitted through the window and into the sample.

In yet other implementations, isolating either the mechanical or the thermal response from the acquired data based on a priori information can also be implemented by using a calibration phantom, of which either the optical absorption or the optical scattering has been characterized.

The disclosed OCT with optical actuation may be operated in a regime where the mechanical response clearly dominates, either by minimizing the thermal absorption or maximizing the mechanical vibration, or both. In one implementation, silicone phantoms can be used because it has been shown to have very low absorption coefficient around the wavelength of the optical scattering force beam. Two soft silicone gels can be made with the compositions of, e.g., 3000 parts and 2500 parts PDMS per 10 parts cross-linker and 1 part curing agent. Based on these compositions, the optical absorption coefficient of the two gels should differ by no more than 0.07%. On the other hand, the mechanical properties of the two gels differed significantly—it could be seen by eye that the 3000 parts PDMS gel was much softer. The experimentally observed displacements in the two gels differed in magnitude by at least 10% at higher frequencies and up to 74% at lower frequencies, suggesting that mechanical response dominated while thermal response contributed very little to the observed displacements. In addition, the frequency-dependent vibration amplitudes follow the trends that would be expected from a viscoelastic material under forced mechanical vibration.

Figure 13:
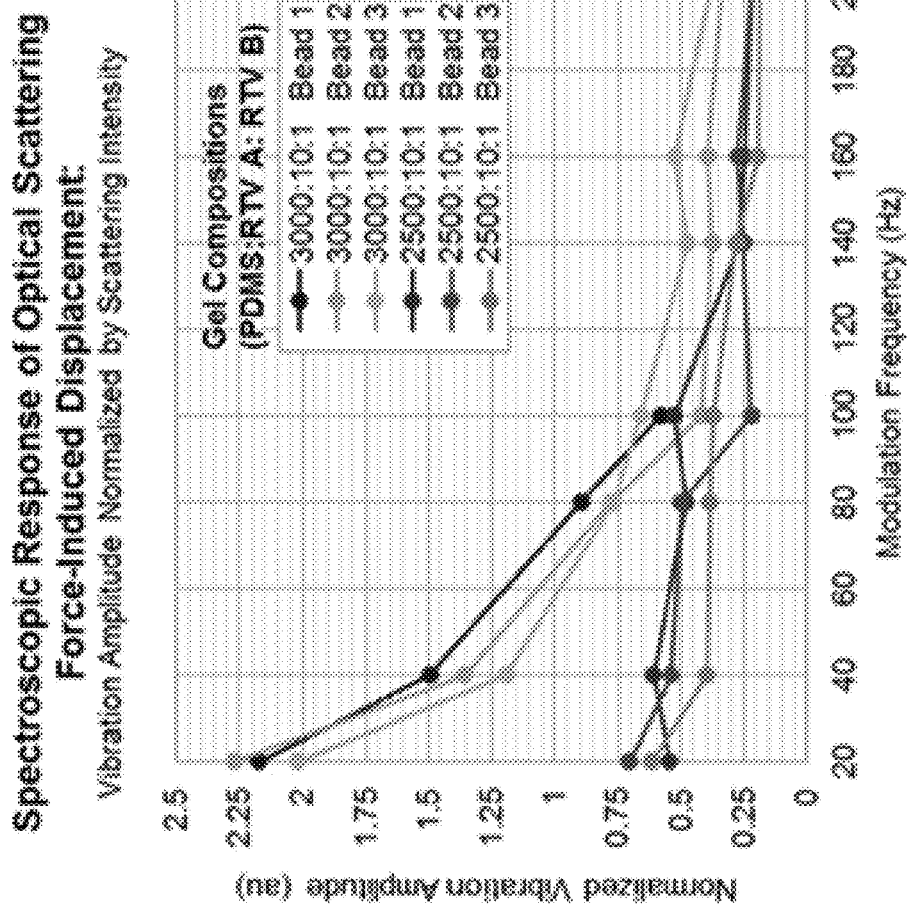
FIG. 13 shows examples of observed vibration amplitude normalized by OCT scattering intensity as a function of optical scattering force modulation frequency for two silicone gel compositions.

FIG. 13 shows examples of observed vibration amplitude normalized by OCT scattering intensity as a function of optical scattering force modulation frequency for two silicone gel compositions. Three measurements from three polystyrene beads were taken independently in each gel. The softer 3000 parts PDMS gel clearly responded with larger vibration amplitude for the same amount of applied optical scattering force. The frequency-dependence of vibration amplitude also showed that the two gels had difference spectroscopic response, as would be expected from two viscoelastic materials with different contribution of viscosity.

The disclosed technology based on OCT for OCE measurements by optical actuation can also improve the sensing performance by using methods of improving the quality of data, both experimental and in post-processing, in the cases where the magnitude of the expected responses may be extremely low, e.g. sub-nanometer displacements. In some situations, displacements induced by optical scattering force may be as low as several tens or hundreds of picometers for certain materials at certain modulation frequencies. In order to accurately detect such small displacements, one or more of the following techniques may be used to mitigate some experimental difficulties and improve the quality of data.

For example, due to chromatic aberration, the foci of the photonic force actuation beam and the OCT imaging beam will focus at different depths in the sample. The misalignment of the two beams disrupts the expected correlation between OCT scattered amplitude and magnitude of displacements, or the signal-to-noise ratio (SNR) of the phase-sensitive OCT signal. In some device designs, it may be desirable to control and adjust the separation in depth between the two foci in order to optimize the quality of acquired signals. This may be accomplished by the use of a variable hyperchromatic objective, which manipulates the focus depth of specific wavelengths of light.

For another example, some OCT implementation may reference the acquired data to a separate control dataset in order to minimize the confounding effects of inherent noises in the system. This may be accomplished by, first, acquiring a normal OCT dataset without the application of the optical scattering force; second, keeping all acquisition parameters constant, acquire a dataset with the application of the optical scattering force; and third, extracting from each dataset the phase information of the backscattered light as Phase of complex time-domain OCT data, Phase difference between every nth line scan, where n may range from 1 to a desired integer number of line scans, or Cumulative sum of the phase difference. Fourth, this processing can numerically subtract the phase information of the normal OCT dataset (with actuation beam turned off) from the optical scattering force dataset.

In other applications, the disclosed technology based on OCT for OCE measurements by optical actuation can be configured as an alternative to non-contact atomic force microscope (AFM) devices to use the optical actuation to probe greater depths than AFM below the target surfaces. In implementations, the disclosed OCT technology with optical actuation can be used for measuring mechanical properties/hydration of contact lenses, or for measuring mechanical properties of other silicone-based biomaterials.

Figure 14:
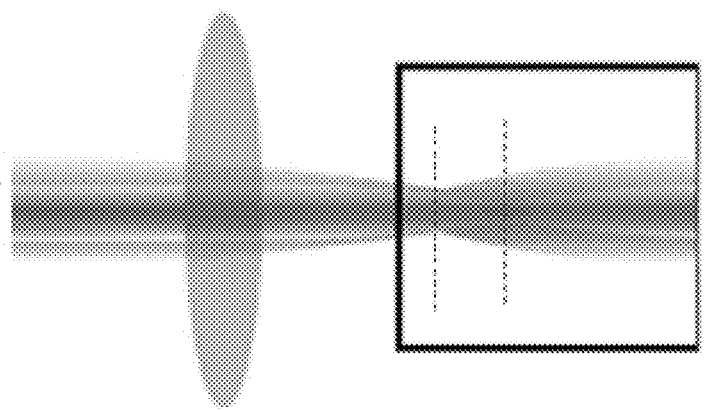
FIG. 14 shows optical adjustment of focal points of both the optical actuation beam and the OCT sampling beam along the axial direction.
Figure 14:
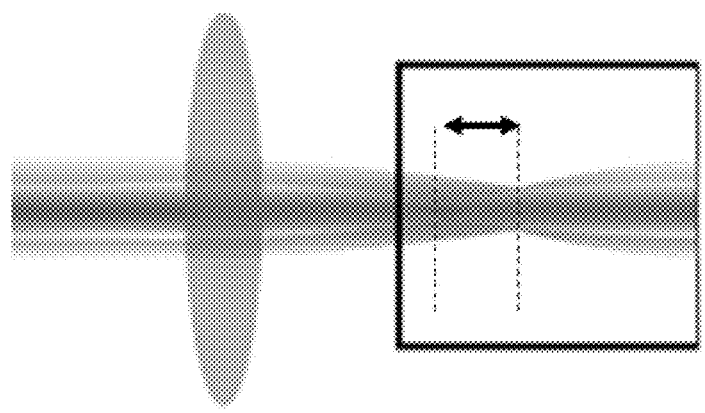

In implementing the above OCT devices based on optical actuation, typical lenses used in the OCT sampling arm tend to have chromatic aberrations so that each lens will form a focus at a different axial location depending on the optical wavelength. This is a problem if the photonic force beam focuses far from the OCT focus since SNR degrades far from the OCT focus. This is particularly a problem if the photonic force focus is below the OCT focus. FIG. 14 illustrates this condition in FIG. 14(a) on the left. In order to overcome this limitation, a variable hyperchromat can be used in place of or in conjunction with the typical objective in the sample arm. A fixed hyperchromat will provide a fixed z-shift to the focus of the optical actuation beam or photonic force (PF) beam; if the PF focus is below the OCT focus, it can be shifted to be above as illustrated in FIG. 14(b) on the right. Additionally, use of a variable hyperchromat can allow the user to tune the separation between the two beams in order to optimize the quality of the PF-OCE data that can be acquired.

The disclosed examples demonstrate displacements induced by optical forces including optical scattering forces and optical gradient forces in viscoelastic and biological media. In some implementations where optical scattering forces rather than gradient forces are used for optical manipulation, a low optical numerical aperture (NA) beam can be used advantageously for OCE to produce a localized force over an extended depth range.

The disclosed technology based on OCT for OCE measurements by optical actuation can be used for a range of applications for diagnosing diseases and other biological and medical sensing applications based on established evidence for the impact of tissue biomechanics on shaping normal biological development and the progression of disease, including the detection of cancerous or atherosclerotic lesions, investigation of ocular biomechanics and its clinical relevance, and studying the inhomogeneity of mechanical properties in skin.

A. Cancer

Stiffness of tissue is widely utilized as a clinical method for the initial detection of tumors. The ability to detect tumors when they are small is crucial to early cancer detection. Due to the unique spatial scale coverage of OCE compared to other techniques, OCE is a promising approach for the diagnosis of early-stage tumors, or the identification of tumor margins with higher accuracy and precision. Surgical removal of the tumor is an important consideration for treatment. Currently, margin analysis of resected tissue is only available postoperatively from histological images. This can result in the need for additional surgeries if the selected margins were not sufficiently large. Intraoperative evaluation of the completeness of surgical tumor excision would benefit from the ability to detect smaller high-risk areas. This may reduce the need for additional surgeries, and help avoid excising large amounts of healthy tissue to ensure complete resection.

B. Atherosclerosis

Atherosclerosis is a vascular disease that occurs in arteries due to the accumulation of lipids, cholesterol, calcium, monocytes and other inflammatory cells. The deposits result in thickening of the arterial wall and form plaques which, upon maturation, are susceptible to rupture. Vulnerable plaques exhibit high strain when subjected to a stress in comparison with healthy tissue; the stress in the fibrous cap of the plaque increases with increased macrophage infiltration and as the probability of rupture increases [121]. Once ruptured, these plaques trigger blood clotting, which can cause occlusion of nearby blood vessels thereby resulting in stroke or myocardial infarction. The disclosed OCT technology based on optical actuation can be used to determine the biomechanical properties of blood vessels for identifying these vulnerable atherosclerotic lesions in coronary arteries.

C. Ocular Biomechanics

Ocular biomechanics plays an important role in the clinical diagnosis of several degenerative ocular diseases including keratoconus and glaucoma. Stiffening of the crystalline lens with age has long been considered to cause presbyopia, however the mechanism by which this occurs is not well understood. In addition, several therapies for ocular dysfunction can modulate the mechanical properties of the cornea, including UV crosslinking and laser therapy used to combat ocular degeneration, and laser vision correction surgery. For these reasons, the study of ocular biomechanics has been a significant driving force in the development of OCE. Perhaps more so than any other application, OCE is particularly suited to the study of ocular mechanics. In addition to micro-scale resolution, this application requires extremely fast (to avoid motion artifacts) and minimally invasive imaging so that the progress of treatments can be tracked over time (collagen cross-linking therapies occur over a period of about an hour). The layered spheroid of the cornea provides a great opportunity to exploit the high axial resolution of OCT and has a comparatively simple geometry (boundary conditions) for mechanical modeling in applying the disclosed OCT technology based on optical actuation. The disclosed OCT technology based on optical actuation may also be used to measure properties of the crystalline lens which possesses a much more complicated geometry due to a depth-dependent gradient index of refraction, and gradient of mechanical properties of the lens.

D. Skin

Biomechanical properties are an important indicator of skin health and disease, structural integrity, cosmesis and aging. Some types of skin cancer (for example: squamous cell carcinomas and malignant melanomas) increase Young's modulus of the skin, while other types of skin cancer (like basal cell carcinomas) decrease Young's modulus. The disclosed OCT technology based on optical actuation can be used to obtain OCE measurements of skin in vivo, e.g., utilizing speckle tracking methods to correlate distinct mechanical properties of skin lesions with the varying degrees of dermal involvement of the lesions, generating mechanical contrast images, or by estimating Young's modulus at different layers, varied hydration conditions and at different skin sites.

E. Other Applications

The disclosed OCT technology based on optical actuation may also be used in various other applications including sensing or monitoring developmental biology and tissue engineering (e.g., measuring microenvironment mechanics associated with cell migration, differentiation and signaling, or measuring the stiffness evaluation of he engineered tissue), measuring cell mechanic such as the change in cellular biomechanical properties in different pathological conditions; measuring mechanical properties of muscle tissue since the function of muscle is highly dependent on mechanical properties and orientation of muscle fibers, measuring properties of the urinary bladder due to the dependence of its biomechanical properties on different pathophysiological conditions, and detecting blood clotting on arterial walls which can trigger cardiovascular events such as myocardial infarction.

Figure 15:
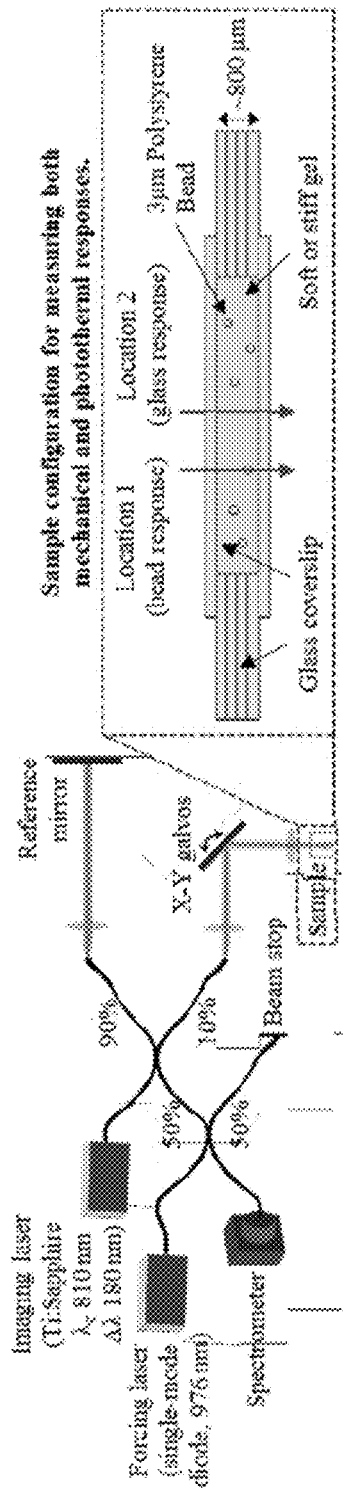
FIG. 15 shows an example of an optical setup and schematic of phantom design illustrating two measurement locations. At location 1, the co-axial beams are aligned to a polystyrene bead. The OPL change measured on the bead reflects the combined mechanical and photothermal responses as the bead is displaced by the forcing beam. At location 2, the co-axial beams are positioned where there is no bead in the beam path. The OPL change measured on the bottom glass coverslip (assumed to be stationary) reflects the photothermal response due to cumulative heating only.

FIG. 15 shows another measurement scheme to distinguish or isolate mechanical and photothermal response from the measured response can be realized from this sandwich sample configuration. By placing the sample into a thin sandwich configuration, confined on top and bottom by stationary glass surfaces, the photothermal response alone can be measured independent of mechanical response. The measured signal from the bead at Location 1 corresponds to the combined mechanical and photothermal responses. The measured signal from the bottom glass surface at Location 2 corresponds to the photothermal response alone, since the glass surface is assumed to be stationary. Subsequently, the mechanical response may be isolated by subtracting the photothermal response.

In another implementation, a plurality of wavelengths is used simultaneously to perturb the sample. Consider the measured oscillatory signal as a linear combination of mechanical and photothermal responses, the mechanical response may be isolated by adding one or more responses, from one or more excitation wavelengths. These wavelengths should correspond to absorption peaks, or be within the window of large absorption coefficient, of the absorbers present in the sample such that photothermal response may be induced with low optical power that any mechanical actuation is negligible. These wavelengths can be modulated at a predetermined amplitude and phase shift relative to that of the actuation wavelength to achieve desirable cancellation (total or partial) of the photothermal response from the actuation wavelength.

Figure 16:
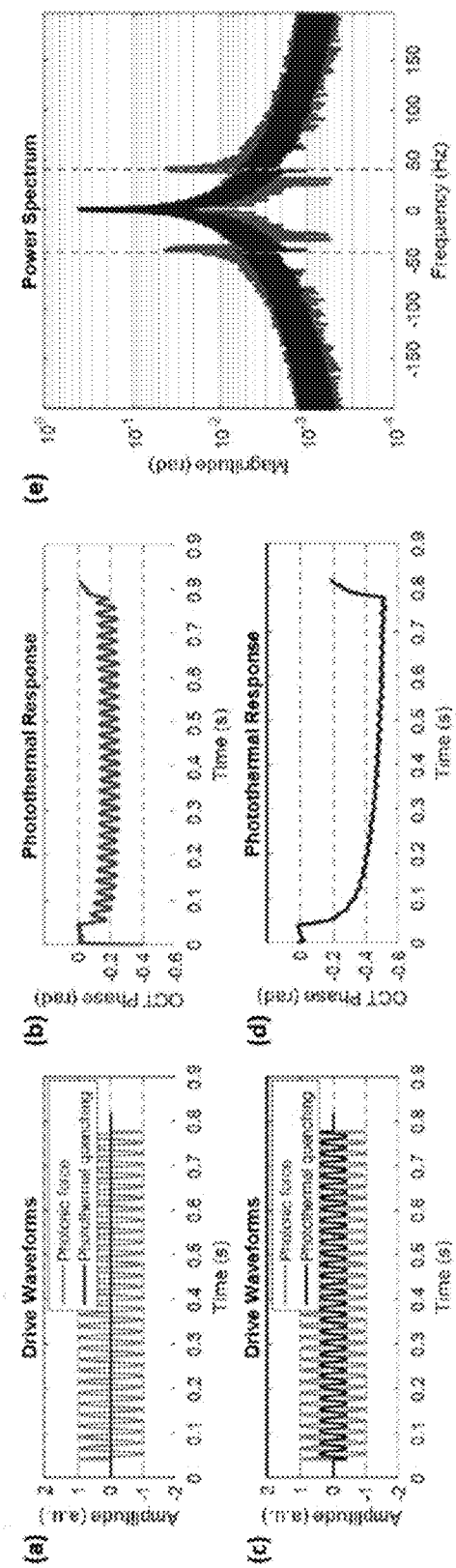
FIG. 16 shows results obtained in one example embodiment of photothermal quenching by using 2 excitation wavelengths. (a-b) Drive waveforms and corresponding measured response for normal excitation with no quenching. (c-d) Drive waveforms and corresponding measured response with photothermal quenching. Note that photothermal quenching drive waveform in (c) is 180 degrees out-of-phase w.r.t. photonic force drive waveform. (d) shows larger magnitude of DC response than (b) due to additional heating by the photothermal quenching wavelength, but the oscillatory response present in (b) has been quenched. (e) Power spectrum of photothermal responses in (b) and (d), showing the disappearance of peaks at the modulation frequency after photothermal quenching.

FIG. 16 shows photothermal response from an implementation in which one photothermal quenching wavelength ($\lambda 2$), with significantly larger absorption coefficient than the actuation wavelength ($\lambda 1$), is used to induce equal magnitude of photothermal response but negligible mechanical actuation. When this $\lambda 2$ is modulated by a drive waveform that is 180 degrees out-of-phase w.r.t. $\lambda 1$ drive waveform, the photothermal response induced by $\lambda 2$ achieves total cancellation the oscillatory photothermal response induced by $\lambda 1$. Thus, any remaining oscillatory response in the measured signal must be induced by the mechanical actuation of $\lambda 1$, since the photothermal response has been quenched.

The plurality of wavelengths may be coupled to the optical system in one or more of the following methods to achieve mechanical actuation and photothermal quenching.

Fiber-Coupling of Plurality of Excitation Wavelengths to SD-OCT System

Figure 17:
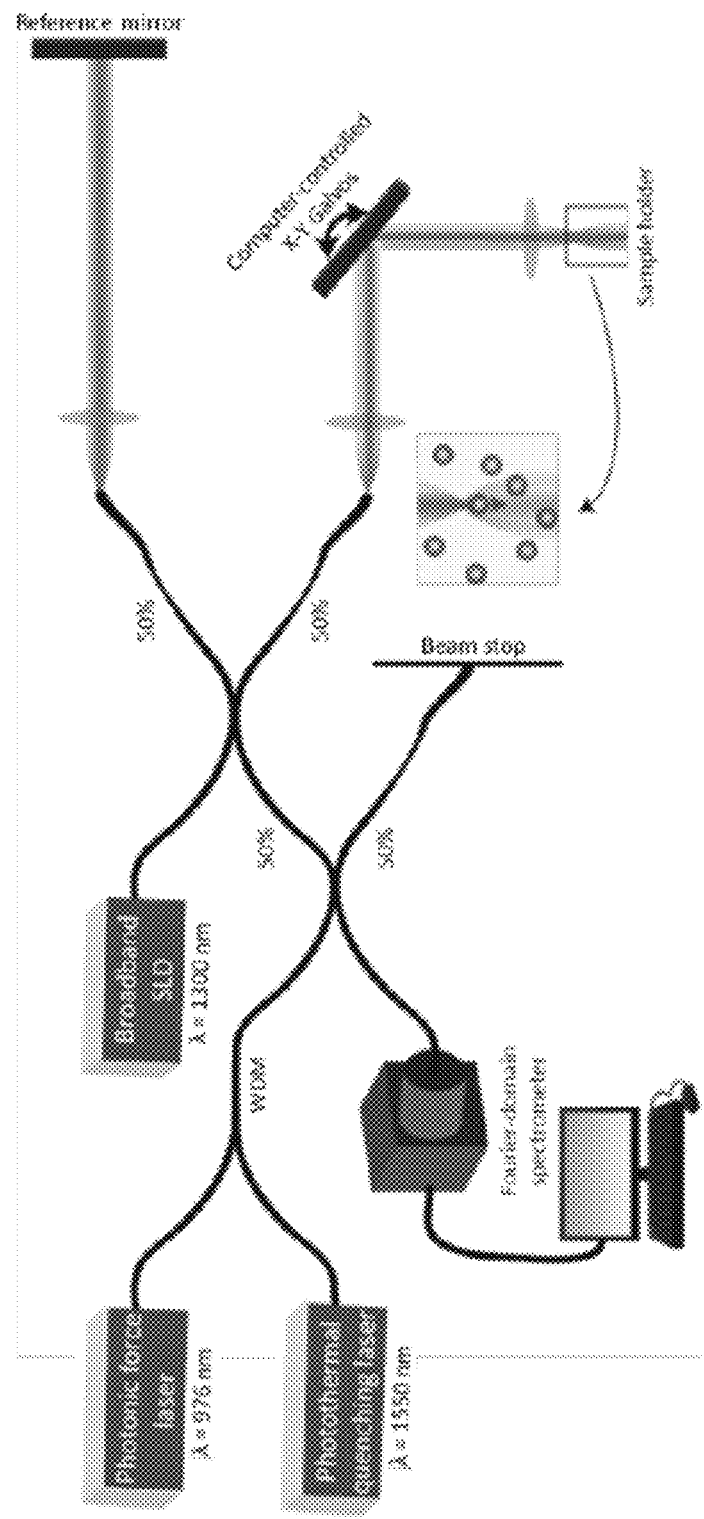
FIG. 17 shows an example schematic of fiber-coupled photonic force OCE with photothermal quenching setup. 976-nm photonic force laser and 1550-nm photothermal quenching laser are combined via a WDM (Thorlabs, WD202A-FC). The combined excitation beam is coupled to the SD-OCT system with 1300-nm light source via a 50:50 fiber coupler.

In some implementations, the photothermal quenching $\mu 2$ is fiber-coupled to the rest of the optical setup via the use of a wavelength division multiplexer (WDM). FIG. 17 shows the schematic of this approach for coupling 976-nm photonic force laser and 1550-nm photothermal quenching laser (designed to specifically quench water absorption in aqueous sample) to the SD-OCT system with 1300-nm light source While the fiber-coupled approach ensures that all three beams (OCT, photonic force, and photothermal quenching) are aligned co-axially in the sample, it may not allow for adjustment different focal depths due to chromatic aberration. In addition, power loss of >80% for the 976-nm photonic force laser is unavoidable due to splitting by the 50:50 coupler and the lossy transmission through 1300 nm single-mode optical fiber.

Free-Space Coupling of Plurality of Excitation Wavelengths to SD-OCT System

Figure 18:
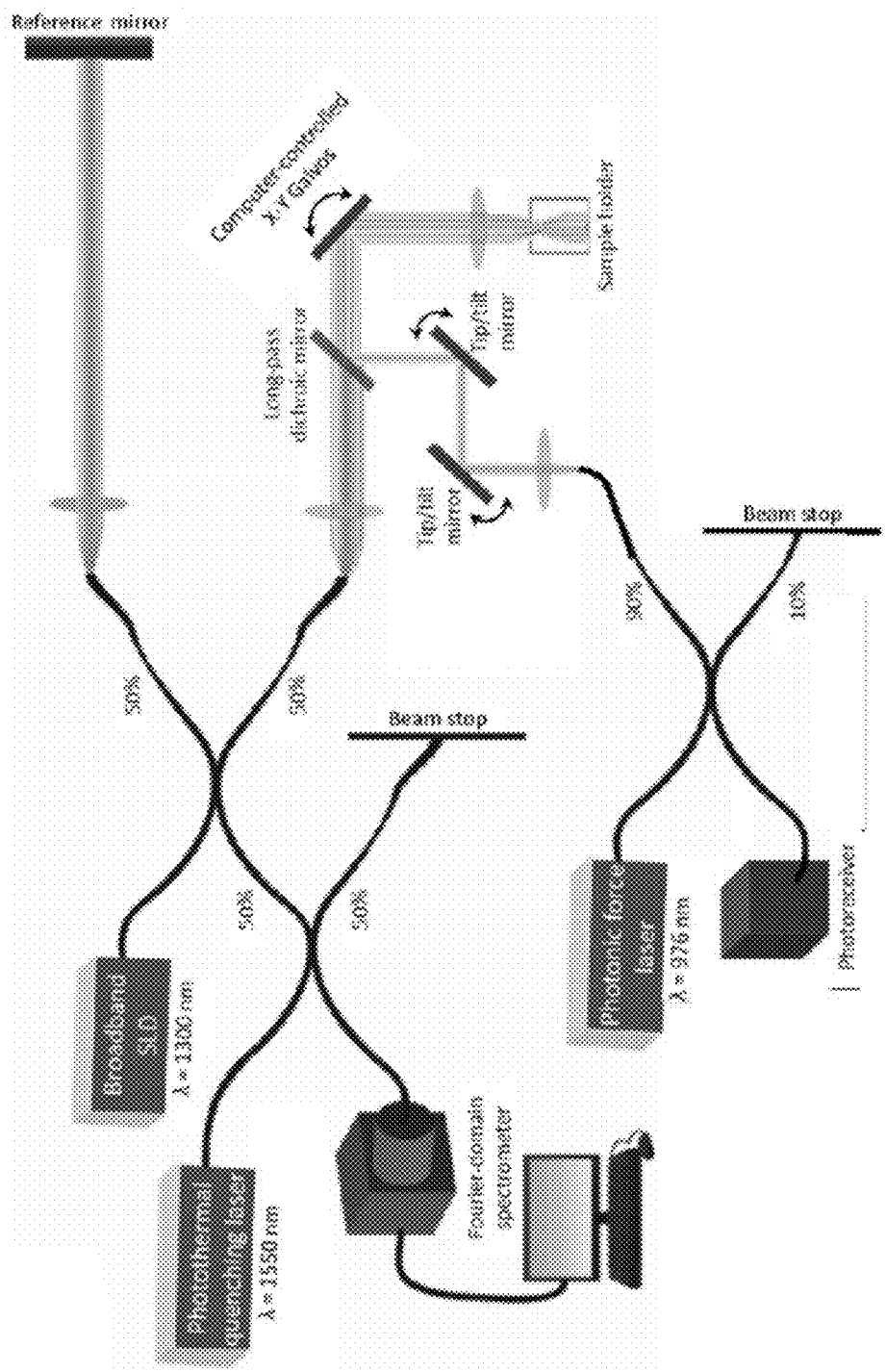
FIG. 18 shows an example schematic of free-space photonic force OCE with photothermal quenching setup. 1550-nm photothermal quenching laser is coupled to SD-OCT system via 50:50 fiber coupler. 976-nm photonic force laser is combined with the OCT and photothermal quenching beams in free-space via a long-pass dichroic mirror. The location of 976-nm beam focal spot is adjusted axially by changing beam collimation and transversely by tip/tilt mirrors.

In some implementations, the photothermal quenching $\zeta 2$ is fiber-coupled to the SD-OCT system via 50:50 coupler, while the photonic force $\lambda 1$ is coupled to the rest of the optical setup in free-space via a long-pass dichroic filter. FIG. 18 shows the schematic of this approach for coupling 976-nm photonic force laser and 1550-nm photothermal quenching laser to the SD-OCT system with 1300-nm light source. This approach avoids transmission power loss for the 976-nm photonic force laser and allows for its focal depth to be adjusted. However, the alignment in the transverse plane must be manually adjusted by the two tip/tilt mirrors while monitoring the confocal signal detected by the photoreceiver.

Figure 19:
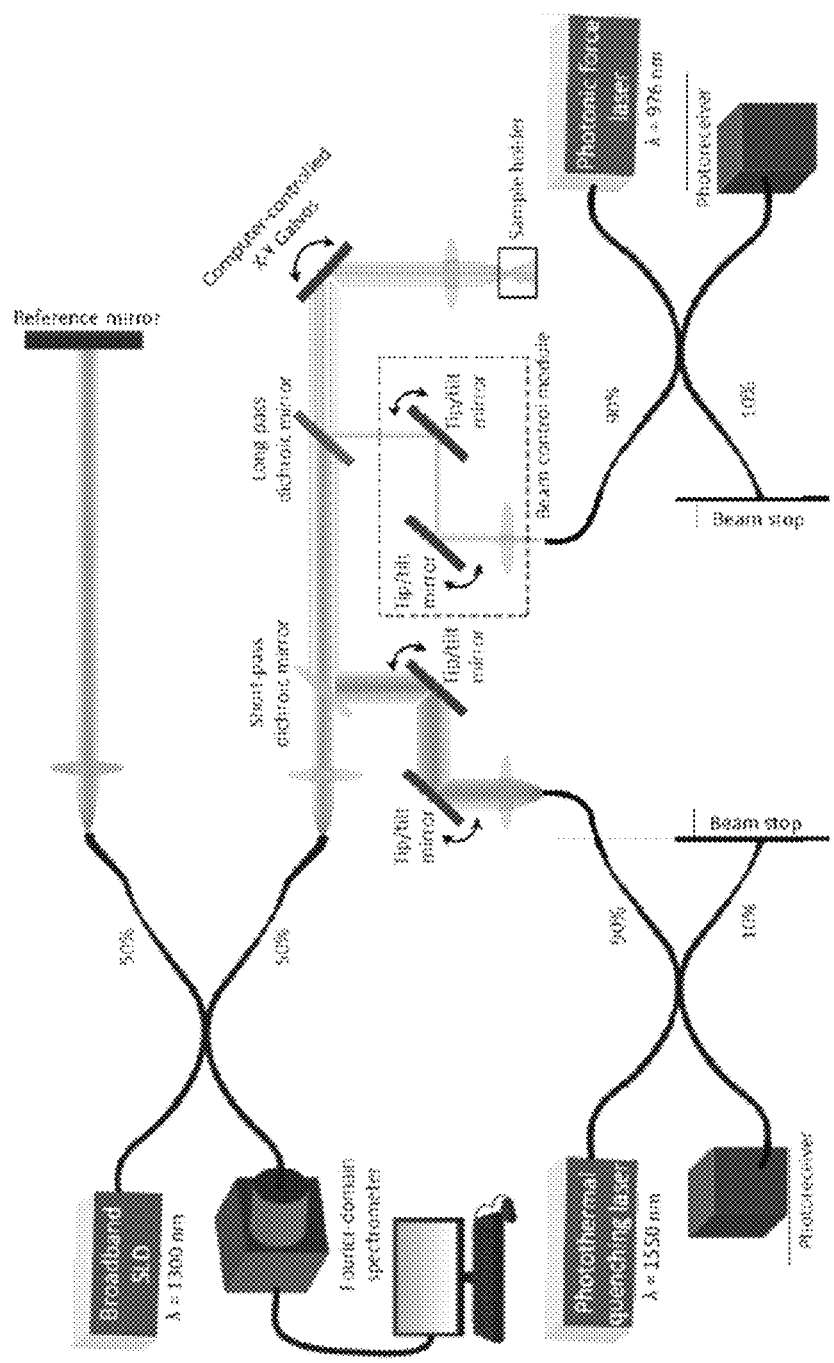
FIG. 19 shows an example schematic of free-space photonic force OCE with both actuation and photothermal quenching beams combined in free-space via dichroic filters. The beam control module allows adjustment of beam aberration and focal spot in 3D space.

If axial adjustment of photothermal quenching focal plane is desirable, the 1550-nm laser can also be combined with the OCT beam in free-space using a similar setup. This is shown in FIG. 19.

In photothermal quenching implementations, it may be desirable to optimize beam quality (aberration control and NA control) and ensure overlap between the focal spots of the multiple beams in 3D space. Aberration control ensures maximum optical power reaches scatterer inside to sample, and NA control enables optimization of optical scattering force for a given scatterer size. The overlap between focal spots in 3D space ensures the mechanical actuation and photothermal quenching is localized to the same excitation volume. In addition, it is desirable to align both mechanical actuation and photothermal quenching beam to the OCT imaging beam in 3D space to optimize OCT signal quality where actuation is maximum.

Figure 20:
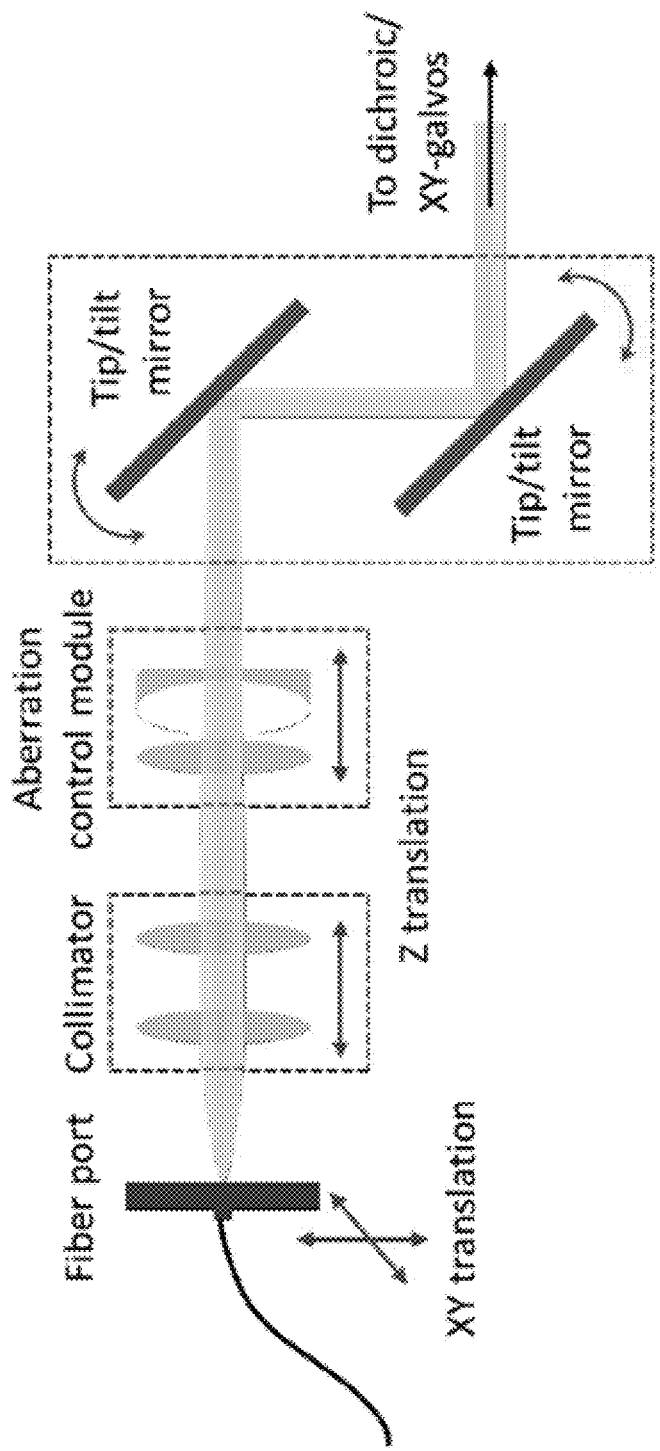
FIG. 20 shows an example schematic of free-space beam control module. The XY translation on the fiber port allows translation of the beam w.r.t. the lenses to minimize aberration. The collimator adjustment allows the translation of the focal spot to desired depth. The aberration control module uses a negative curvature surface to compensate for the positive spherical aberration from other lens components. The tip and tilt mirrors allow translation of the focal spot in the transverse plane.

FIG. 20 shows an implementation of free-space beam control module that provides the ability to adjust transverse and depth of focal spot, beam NA, and beam spherical aberration. This module is to be placed as indicated by the dashed box in FIG. 19.

As described herein, techniques for PF-OCE may be implemented via photothermal AC-component quenching. In some embodiments, the 1550 nm laser is used to quench the photothermal AC contribution from the 976 nm contribution by modulating the contribution. In some embodiments, the 1550 nm beam is configured to have antiphase to the 976 nm beam to produce a 1550 nm PT (photothermal) response that exactly cancels the 976 nm PT response.

Figure 21:
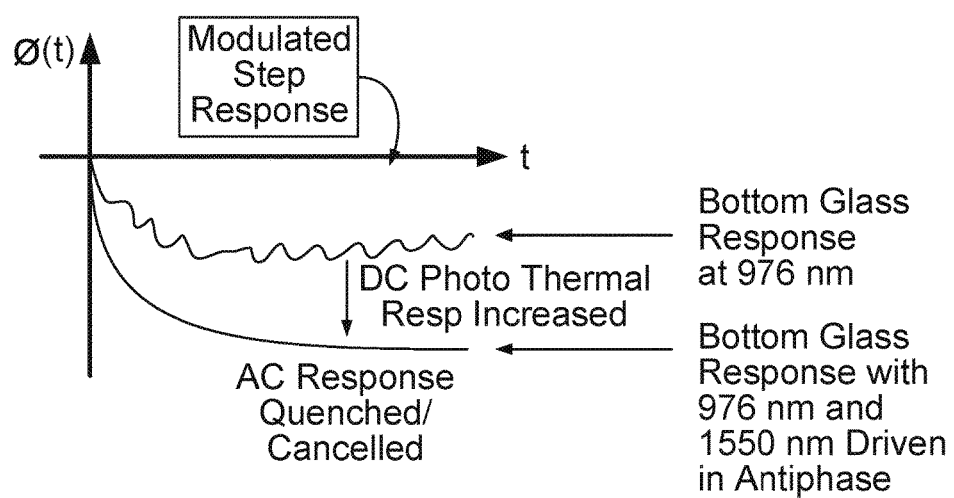
FIG. 21 is a graph showing example optical AC and DC response of an embodiment.

FIG. 21 is a graph showing example optical AC and DC response, e.g., example embodiments depicted in FIG. 15. The graphs shows the change in response when a plurality of wavelengths are used as a light source.

Figure 22:
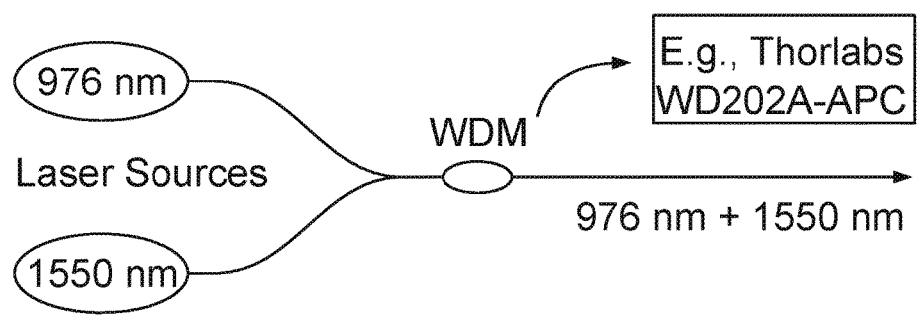
FIG. 22 shows an example light source generator for a plurality of wavelengths.

FIG. 22 shows an example light source generator for a plurality of wavelengths. In this example, a 976 nm source and a 1550 nm source are wavelength division multiplexed using a suitable equipment such as a Thorlabs WD202A-APC, to generate a light source comprising a plurality of wavelengths.

While this patent document contains many specifics, these should not be construed as limitations on the scope of any disclosed methods or of what may be claimed, but rather as descriptions of features that may be specific to particular embodiments of particular disclosed methods. Certain features that are described in this patent document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Only a few implementations and examples are described and other implementations, enhancements and variations can be made based on what is described and illustrated in this patent document.

What is claimed is:

1. A method for sensing a sample based on optical actuation of the sample, comprising:
    operating an optical coherence tomography (OCT) device to obtain optical images of a sample based on optical interference of an optical sampling beam interacting with an optical sample and an optical reference beam from an OCT light source emitting light within an optical spectral band of different optical wavelengths;
    operating a light source to produce an optical actuation beam comprising a plurality of wavelengths, at least one of which is different from a wavelength of the light of the OCT light source, and wherein the optical actuation beam includes a first beam at an actuation wavelength and a second beam at a quenching wavelength; and
    directing the optical actuation beam along with the optical sampling beam to the sample to actuate particles or structures in the sample so that the optical imaging captures information of the sample under the optical actuation.

2. The method as in claim 1, comprising modulating the optical actuation beam using a drive waveform.

3. The method as in claim 2, wherein the optical actuation beam is modulated in amplitude or power.

4. The method as in claim 1, further comprising processing optical imaging information from OCT device output based on varying mechanical properties of different sample materials to distinguish one sample material from another.

5. The method as in claim 1, further comprising processing optical imaging information from OCT device output based on varying optical scattering properties of different sample materials to distinguish one sample material from another.

6. The method as in claim 1, further comprising processing optical imaging information from OCT device output based on varying optical absorption properties of different sample materials to distinguish one sample material from another.

7. The method as in claim 1, further comprising processing optical imaging information from OCT device output based on varying optical actuation schemes or OCT imaging schemes or both to distinguish responses from mechanical properties from optical absorption properties.

8. The method as in claim 1, comprising rendering the OCT imaging beam at an optical wavelength different from an optical wavelength of the optical actuation beam.

9. The method of claim 2, further including modulating the second beam at the quenching wavelength by a waveform that is 180 degrees out-of-phase with respect to the drive waveform.

10. The method of claim 1, wherein the quenching wavelength is greater than the actuation wavelength, thereby having an absorption coefficient larger than that for the actuation wavelength.

11. The method of claim 1, wherein the quenching wavelength is selected to quench water absorption for the sample that is aqueous.

12. The method of claim 1, further including coupling the quenching wavelength to the OCT device using a 50:50 fiber coupler.

13. A system for providing optical actuation and optical sensing, comprising:
an OCT light source configured to provide an optical coherence tomography (OCT) imaging beam into an OCT device positioned to split the OCT imaging beam into an optical sampling beam and an optical reference beam;
a light source generator configured to produce an optical actuation beam comprising a plurality of wavelengths that is coupled along with the optical sampling beam to be directed to a sample to actuate particles or structures in the sample so that the optical imaging captures information of the sample under the optical actuation; wherein the optical actuation beam includes a first beam at an actuation wavelength and a second beam at a quenching wavelength; and
an optical imaging device configured to capture an image of the sample based on optical interferometry.

14. The system of claim 13, wherein the light source that produces the optical actuation beam is coupled to the system using a fiber coupling or a free-space coupling.

15. The system of claim 13, further including a wavelength division multiplexer that combines the first beam at the actuation wavelength and the second beam at the quenching wavelength.

16. The system of claim 13, wherein the first beam at the actuation wavelength is modulated by a drive waveform.

17. The system of claim 16, wherein the second beam at the quenching wave is modulated by another waveform that is 180 degrees out-of-phase with respect to the drive waveform.

18. The system of claim 13, wherein the quenching wavelength is greater than the actuation wavelength, thereby having an absorption coefficient larger than that for the actuation wavelength.

19. The system of claim 13, wherein the quenching wavelength is designed to quench water absorption for the sample that is aqueous.

20. The system of claim 13, further including a 50:50 fiber coupler that is configured to couple the quenching wavelength with the system.

* * * * *